US008406849B2

(12) United States Patent  (10) Patent No.: US 8,406,849 B2
Jeong et al.  (45) Date of Patent: Mar. 26, 2013

(54) SYSTEMS AND METHODS FOR MAGNETIC RESONANCE IMAGING

(75) Inventors: Eun-Kee Jeong, North Salt Lake City, UT (US); Dennis L. Parker, Centerville, UT (US); Kim Seong-Eun Choi, Salt Lake City, UT (US); Evgueni G. Kholmovski, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1575 days.

(21) Appl. No.: 11/732,382

(22) Filed: Apr. 2, 2007

(65) Prior Publication Data

US 2007/0249929 A1 Oct. 25, 2007

Related U.S. Application Data

(60) Provisional application No. 60/788,533, filed on Mar. 31, 2006.

(51) Int. Cl.
*A61B 5/05* (2006.01)
(52) U.S. Cl. ........ 600/410; 600/407; 600/413; 324/300; 324/307; 324/309
(58) Field of Classification Search .................. 600/410, 600/413; 324/300, 307, 309
See application file for complete search history.

(56) References Cited

U.S. PATENT DOCUMENTS

| | | | |
|---|---|---|---|
| 5,492,123 A | 2/1996 | Edelman | |
| 5,873,825 A | 2/1999 | Mistretta et al. | |
| 6,185,447 B1 | 2/2001 | Alley et al. | |
| 6,400,151 B1 | 6/2002 | Haase et al. | |
| 6,445,184 B1 | 9/2002 | Tanttu | |
| 6,492,811 B1 | 12/2002 | Foxall | |
| 6,614,226 B2 | 9/2003 | Wedeen | |
| 6,618,605 B1 * | 9/2003 | Wolff et al. | 600/410 |
| 6,842,000 B2 | 1/2005 | Norris et al. | |
| 6,891,373 B2 | 5/2005 | Deimling | |
| 7,109,707 B2 | 9/2006 | Griffin | |
| 2002/0022778 A1 | 2/2002 | Wiese et al. | |
| 2003/0076098 A1 | 4/2003 | Steinhoff et al. | |
| 2004/0064035 A1 | 4/2004 | Miyoshi et al. | |
| 2004/0071324 A1 | 4/2004 | Norris et al. | |
| 2005/0110489 A1 | 5/2005 | Miyoshi | |
| 2005/0168221 A1 | 8/2005 | Miyoshi | |
| 2006/0039856 A1 | 2/2006 | Cowan et al. | |
| 2006/0161060 A1 | 7/2006 | Pai | |
| 2007/0016000 A1 | 1/2007 | Prince et al. | |

OTHER PUBLICATIONS

Jeong et al. (High-Resolution Diffusion-Weighted 3D MRI, Using Diffusion-Weighted Driven-Equilibrium (DW-DE) and Multishot Segmented 3D-SSFP Without Navigator Echoes), Magnetic Resonance in Medicine, vol. 50, pp. 821-829, 2003.*
Xiangeng Shi, et al., "Single-Shot T1 Mapping Using Simultaneous Acquisitions of Spin- and Stimulated-Echo-Planar Imaging (2D ss-SESTEPI)", Magnetic Resonance in Medicine 64:734-742 (2010).

* cited by examiner

*Primary Examiner* — Unsu Jung
*Assistant Examiner* — Joseph M Santos
(74) *Attorney, Agent, or Firm* — Alexander J Burke

(57) ABSTRACT

Methods and apparatus for operating an MRI system is provided. The disclosure provides a diffusion-prepared driven-equilibrium preparation for an imaging volume and acquiring 3-dimensional k-space data from said prepared volume by a plurality of echoplanar readouts of stimulated echoes. An excitation radio-frequency signal and first and second inversion RF signals are provided to define a field-of-view (FOV).

12 Claims, 20 Drawing Sheets

SYSTEMS AND METHODS FOR MAGNETIC RESONANCE IMAGING

CROSS-REFERENCE TO RELATED APPLICATIONS

This application claims the benefit under 35 U.S.C. §119 (e) of U.S. Provisional Patent Application No. 60/788,533, filed on Mar. 31, 2006, and titled "SYSTEMS AND METHODS FOR MAGNETIC RESONANCE IMAGING," the entirety of which is hereby incorporated by reference.

GOVERNMENT LICENSE RIGHTS

The U.S. Government has a paid-up license in this invention and the right in limited circumstances to require the patent owner to license others on reasonable terms as provided for by the terms of Grant Nos. R21 NS052424, R21 EB005705, and R01 HL57990 awarded by the National Institutes of Health.

BACKGROUND OF THE INVENTION

1. Field of the Invention

This application relates to magnetic resonance imaging.

2. Description of the Related Art

Diffusion-weighted magnetic resonance (MR) imaging (DWI) is a known tool for detecting abnormal water diffusion in the brain (e.g., ischemic stroke). The directional information obtained using diffusion tensor MRI (DTI) is valuable in understanding as well as evaluating white matter abnormalities in neurological diseases, such as Alzheimer disease, schizophrenia, multiple sclerosis, and neurofibromatosis. DWI and DTI may also give useful information about the development and disorders of ordered structures in extracranial organs such as the heart, kidney, breast, and prostate.

Although DTI can provide useful information about white-matter diseases in the brain, high resolution DTI of brain regions near the temporal bone or sinuses, of small neural structures such as the spinal cord or optic nerve, or of extracranial organs in vivo has been difficult to achieve using conventional two-dimensional (2D) singleshot diffusion-weighted EPI techniques (2D ss-DWEPI). There are strong non-uniform local magnetic fields created by the magnetic susceptibility changes at tissue/bone or tissue/air interfaces, which typically induce severe distortion on the resultant ss-DWEPI images. The amount of susceptibility induced geometric distortion is proportional to the total sampling time in EPI. Typically, increasing spatial resolution requires an increase in the duration of the data acquisition window, which in turn increases the distortion from off-resonance effects. As a result, the spatial resolution obtained using conventional 2D ss-EPI is generally much lower than that obtainable with conventional, multi-shot MRI, giving decreased resolution for measurements of interest, such as white matter tract anatomy and nerve fiber anatomy. For these reasons, 2D ss-DWEPI has been clinically useful only for moderately low resolution intracranial applications. EPI with parallel imaging has been successfully applied to high-resolution brain DWI and DTI studies resulting in substantial image quality improvement.

There are several non-EPI singleshot DWI techniques, which include multiple spin-echo sequences (e.g., ss-FSE (or HASTE) and GRASE), STEAM, and fast gradient echo sequences (FLASH), that complete the total data acquisition following a single diffusion weighting. These 2D sequences typically acquire slightly more than half of the $k_y$ encodings in about 500 ms after a single diffusion weighting preparation. These non-EPI singleshot techniques typically employ relatively thick slices to overcome their intrinsic low SNR.

Multishot imaging techniques may be used to increase SNR, improve spatial resolution and reduce susceptibility induced artifacts. However most multishot DWI acquisition techniques suffer from the instability of phase errors among shots due to global or localized motions during application of the large diffusion gradients. There has been reasonable success with techniques that use navigator echoes to detect and correct phase errors, or that use non-singleshot-EPI approaches that are less sensitive to phase errors. Because most of these are 2D acquisition techniques, they produce relatively poor resolution along the slice direction.

SUMMARY OF THE INVENTION

Certain embodiments of the present disclosure relate to methods and apparatus for operating an MRI system. The disclosure provides a diffusion-prepared driven-equilibrium preparation for an imaging volume, and acquiring 3-dimensional k-space data from the prepared volume by a plurality of echoplanar readouts of stimulated echoes.

In certain embodiments, the diffusion-prepared driven-equilibrium preparation includes a single diffusion-prepared driven-equilibrium preparation. In certain embodiments, the 3-dimensional k-space data includes a raw data that has not been transformed. In certain embodiments, the MRI system is operated for diffusion-weighted MR imaging (DWI). In certain embodiments, the MRI system is operated for diffusion tensor MR imaging (DTI). In certain embodiments, the acquiring of 3-dimensional k-space data includes acquiring substantially entire 3-dimensional k-space data.

Certain embodiments of the present disclosure relate to a method for interleaved MR imaging. The method includes providing an excitation radio-frequency (RF) signal, and providing first and second inversion RF signals to define a field-of-view (FOV).

In certain embodiments, the first and second inversion RF signals include first and second inversion RF pulses. In certain embodiments, the first inversion RF pulse is applied substantially immediately after the excitation RF signal. In certain embodiments, the first and second inversion RF pulses are separated by a time approximately 5 ms or larger. In certain embodiments, the method further includes providing slice-selective gradients that are selected such that magnetization within the FOV is substantially preserved while magnetization external to the FOV is substantially suppressed, thereby allowing magnetization in each of a plurality of slices to be substantially maintained in its equilibrium state while exciting and imaging one or more others of the plurality of slices.

Certain embodiments of the present disclosure relate to a method for correcting a motion artifact during MR imaging. The method includes acquiring navigation data substantially together with imaging data. The method further includes determining whether to re-acquire the imaging data based on the navigation data. The method further includes re-acquiring the imaging data based on the determination.

In certain embodiments, the motion artifact is due to intra-shot motion. In certain embodiments, the motion artifact is due to inter-shot motion. In certain embodiments, the determining and re-acquiring are performed substantially real-time. In certain embodiments, the navigation data includes 2D k-space navigation echoes, and the determining includes identifying value and position of the largest signal in the 2D k-space to see if either of the value or position is outside of a corresponding selected range. In certain embodiments, the MR imaging includes a multi-average singleshot EPI operated as at least one of DWI, DTI, and fMRI. In certain embodiments, the MR imaging includes at least one of spin-echo, multiple spin-echo, gradient-echo, and segmented gradient-echo.

Certain embodiments of the present disclosure relate to a control system for an MRI apparatus. The system includes a control component configured to generate one or more instructions for providing diffusion-prepared driven-equilibrium preparation for an imaging volume, and acquiring a substantially entire 3-dimensional k-space data from the prepared volume by a plurality of echoplanar readouts of stimulated echoes.

In certain embodiments, the diffusion-prepared driven-equilibrium preparation includes a single diffusion-prepared driven-equilibrium preparation. In certain embodiments, the 3-dimensional k-space data includes a raw data that has not been transformed. In certain embodiments, the MRI apparatus is for diffusion-weighted MR imaging (DWI). In certain embodiments, the MRI apparatus is configured for diffusion tensor MR imaging (DTI). In certain embodiments, the acquiring of 3-dimensional k-space data includes acquiring substantially entire 3-dimensional data.

In certain embodiments, the control component includes one or more devices. In certain embodiments, a single device is configured to generate the one or more instructions. In certain embodiments, a plurality of devices are configured to generate the one or more instructions.

Certain embodiments of the present disclosure relate to a control system for an MRI apparatus. The system includes a control component configured to generate one or more instructions for providing an excitation radio-frequency (RF) signal, and providing first and second inversion RF signals to define a field-of-view (FOV).

In certain embodiments, the first and second inversion RF signals include first and second inversion RF pulses. In certain embodiments, the first inversion RF pulse is applied substantially immediately after the excitation RF signal. In certain embodiments, the first and second inversion RF pulses are separated by a time approximately 5 ms or larger. In certain embodiments, the one or more instructions further includes an instruction for providing slice-selective gradients that are selected such that magnetization within the FOV is substantially preserved while magnetization external to the FOV is substantially suppressed, thereby allowing magnetization in each of a plurality of slices to be substantially maintained in its equilibrium state while exciting and imaging one or more others of the plurality of slices.

In certain embodiments, the control component includes one or more devices. In certain embodiments, a single device is configured to generate the one or more instructions. In certain embodiments, a plurality of devices are configured to generate the one or more instructions.

Certain embodiments of the present disclosure relate to a system for correcting a motion artifact during MR imaging. The system includes a control component configured to generate one or more instructions for acquiring navigation data substantially together with imaging data, determining whether to re-acquire the imaging data based on the navigation data, and re-acquiring the imaging data based on the determination.

In certain embodiments, the motion artifact is due to intra-shot motion. In certain embodiments, the motion artifact is due to inter-shot motion. In certain embodiments, the determining and re-acquiring are performed substantially real-time. In certain embodiments, the navigation data includes 2D k-space navigation echoes, and the determining includes identifying value and position of the largest signal in the 2D k-space to see if either of the value or position is outside of a corresponding selected range. In certain embodiments, the MR imaging includes a multi-average singleshot EPI operated as at least one of DWI, DTI, and fMRI. In certain embodiments, the MR imaging includes at least one of spin-echo, multiple spin-echo, gradient-echo, and segmented gradient-echo.

In certain embodiments, the control component includes one or more devices. In certain embodiments, a single device is configured to generate the one or more instructions. In certain embodiments, a plurality of devices are configured to generate the one or more instructions.

For purposes of summary, certain aspects, advantages, and novel features have been described herein. It is to be understood that not necessarily all such advantages may be achieved in accordance with any particular embodiment. Thus, this disclosure may be embodiment or carried out in a manner that achieves or optimizes one advantage or group of advantages as taught herein without necessarily achieving other advantages as may be taught or suggested herein.

BRIEF DESCRIPTION OF THE DRAWINGS

A general architecture that implements the various features of the disclosure will now be described with reference to the drawings. The drawings and the associated descriptions are provided to illustrate embodiments of the disclosure and not to limit the scope of the disclosure. Throughout the drawings, reference numbers are re-used to indicate correspondence between referenced elements.

DETAILED DESCRIPTION OF EXEMPLARY EMBODIMENTS

Figure 1:
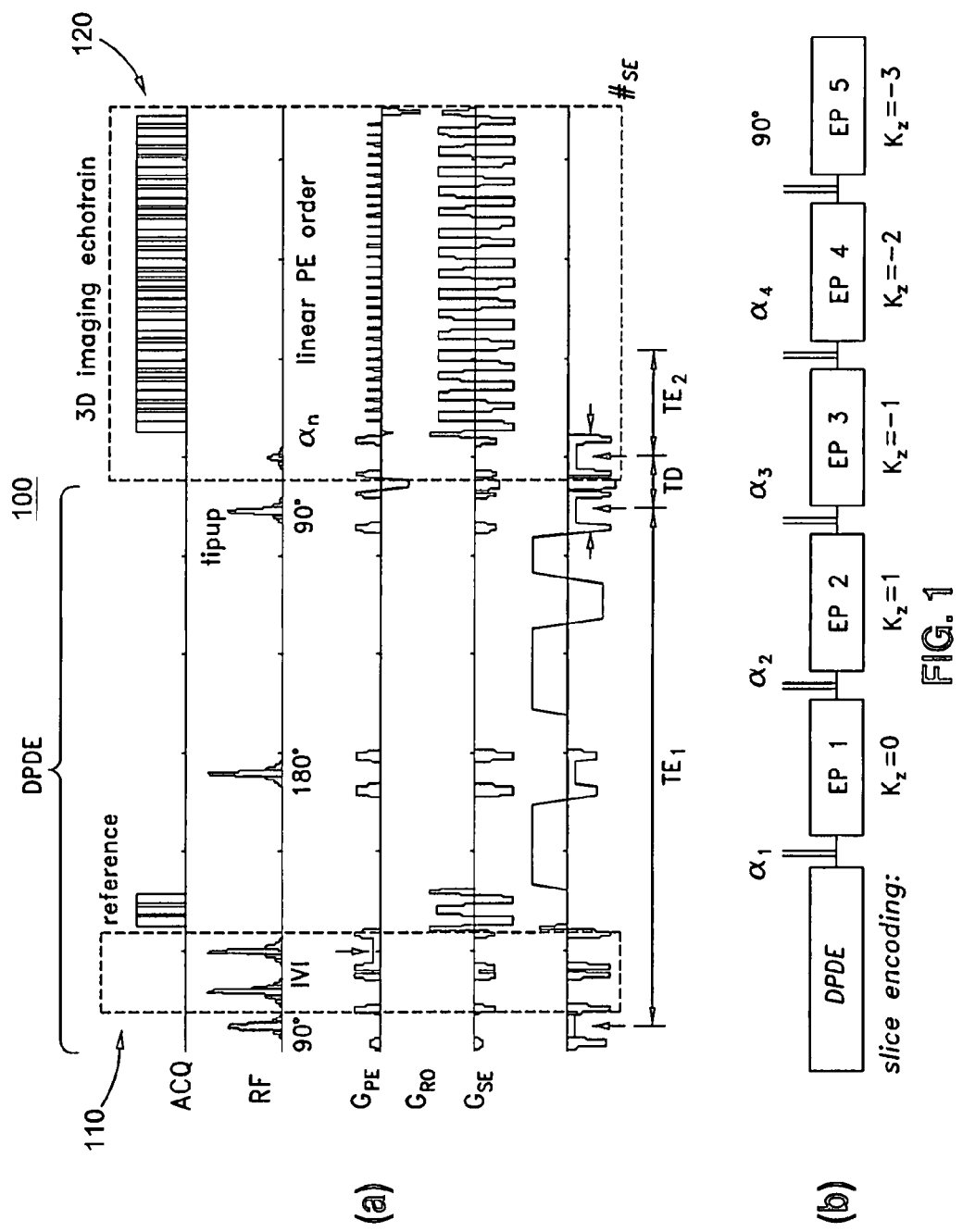
FIG. 1 depicts a 3D Single Step Echo-Planar Imaging pulse sequence.

An improved three-dimensional (3D) singleshot stimulated echo planar imaging (3D ss-DWSTEPI or ss-STEPI or STEPI) is presented which includes a novel technique to perform 3D singleshot DWI and DTI of a restricted 3D volume. In certain embodiments, 3D ss-DWSTEPI acquires 3D raw data from a limited 3D volume after a single diffusion-prepared driven-equilibrium (DPDE) preparation by short EPI readouts of several stimulated echoes. In certain embodiments, the raw data includes k-space data. In certain embodiments, the raw data includes data that has not undergone any transformation. The EPI readout time is preferably shortened by using an inner volume imaging (IVI) technique along the phase-encoding direction.

In certain embodiments, 3D ss-STEPI may be used to image any localized anatomical volume within a body without aliasing artifact and with high-resolution. The results from 3D ss-STEPI imaging studies of phantoms, an excised animal heart, and in vivo results from human volunteers, all demonstrated excellent resolution among all directions. In certain embodiments, the advantages of STEPI versus existing techniques for DTI include: (1) no motion-induced artifact, (2) much reduced susceptibility artifact, (3) high spatial resolution in all imaging directions, and (4) reduced scan time. STEPI can be also used in multishot EPI imaging to reduce the total imaging time by a factor equal to the number of slice-encodings.

In certain embodiments, a method for interleaved multiple inner volume imaging (IMIVI) uses two inversion (180 degree) RF pulses to define the desired FOV. In certain embodiments, the inversion pulses are applied immediately after the excitation RF pulse and are separated by as little as about 5 ms. In some embodiments, the inversion pulses are separated by more than about 5 ms, and in some embodiments, the inversion pulses are separated by less than about 5 ms. In certain embodiments, the slice selective gradients applied with the RF pulses are chosen such that magnetization from within the total volume imaged is preserved, while the magnetization external to the imaged volume is completely suppressed. Thus, the magnetization in each slices or slab is only slightly disturbed from its equilibrium state while exciting an imaging the other slices or slabs. As a result, the signal loss for all slices is minimal allowing time efficient interleaved multislice/slab acquisition.

In some embodiments, real-time navigation (RTN) determines if the data acquired by any specific EPI readout is corrupted by the subject's motion, and instructs the MRI scanner to reject and reacquire the data. 2D navigator echoes can be acquired as a part of the data acquisition process, and then sent to the data processing computer where they are analyzed by identifying the value and the position for the largest signal n k-space data of the navigator. If the magnitude or the position of the peak is out of bounds, the data are rejected and the data acquisition program is instructed to reacquire the data in real time. RTN can be useful for any MR imaging techniques, especially for multi-average singleshot EPI (DWI, DTI, and fMRI). It can be useful for most conventional MR imaging techniques, which include (but are not limited to) spin-echo, multiple-spin-echo (fast-/turbo-spin-echo), gradient-echo (SPGR/GRASS, FLASH/FISP, field-echo), segmented gradient-echo (MP-RAGE).

FIG. 1 depicts a 3D ss-DWSTEPI pulse sequence 100. Pulse signal 100 includes two main sections, a diffusion-prepared driven-equilibrium (DPDE) preparation section 110 and a 3D data acquisition section 120. Pulse sequence 100 comprises digital sampling of MR signals, depicted in FIG. 1 as ACQ, an RF signal, a phase encoded gradient signal $G_{PE}$, readout gradient signal $G_{RO}$, and slice encoded gradient signal $G_{SE}$.

As depicted in FIG. 1, DPDE preparation section 110 precedes the stimulated echo imaging sequence. Two 180° RF pulses are applied following a 90° excitation pulse. The 180° pulses are used to determine the localized volume for interleaved multiple inner volume imaging. The first inversion of the double inversion is used to invert substantially all magnetization, and ultimately substantially eliminate unwanted signal from the out-of-volume magnetization. The second inversion is used to restore the magnetization in other slabs to be imaged and allows time-efficient interleaved acquisition of multiple slabs. The earliest group of ACQs between the double inversion and the first diffusion gradient collects three reference echoes (2 odd and 1 even echo) for EPI phase correction. Before being tipped up to the longitudinal direction, the diffusion-prepared transverse magnetization in each voxel is dephased more than $2\pi$ by a dephasing gradient (indicated by right arrow: → in FIG. 1a) to remove the image intensity dependence upon the tipup RF pulse phase. The residual transverse magnetization is suppressed by a spoiler gradient applied after the tipup pulse. The slice-selection gradient (indicated by the vertical arrow in section (a)) is applied in the slice-encoding direction for substantially all RF pulses in DPDE preparation, except for the two IVI refocusing/inversion RF pulses, where the first pulse is spatially non-selective and the gradient for the second 180° pulse is applied along the phase-encoding direction to define the reduced phase FOV.

IVI limits the excited FOV in the phase-encoding (PE) direction to include only the anatomy of interest. Time efficient interleaved multivolume IVI can be obtained because the two refocusing pulses with slice selection along the phase encoding direction that are used to create the limited FOV also return most of the out-of-slab magnetization to the longitudinal direction.

The data acquisition part of the pulse sequence includes multiple segments (section (b)). Each segment includes the excitation RF pulse (creating a single stimulated echo), rephasing crusher gradient, EPI readout, and rewinding gradients. For each segment, the flip angle of the imaging RF pulses is gradually increased to reduce the $T_1$ decay-related blurring in the slice direction. The flip angle for the last segment is 90° to consume substantially all remaining longitudinal DW magnetization. The rephasing crusher gradient (indicated by left arrow: ← in FIG. 1), applied substantially immediately after the slice selection gradient of excitation RF pulse, α, rephases the phase accumulated during the dephasing crusher gradient (→) prior to the tipup 90° RF pulse. The ETL of the EPI readout in each segment is chosen to be substantially the same as the number of acquired $k_y$ phase-encodings (e.g., 31 for an imaging matrix with 48 $k_y$ views). This number is kept relatively small to reduce susceptibility artifacts. The phase-encoding order is increased linearly in each segment, and a center-out slice encoding order is used to improve the SNR by placing the center of slice-encoding at the earliest echotrain acquisition. In one example, 62.5% of both phase-encodings and slice-encodings ($k_y$ and $k_z$, respectively) are asymmetrically acquired to reduce the ETL and the length of the total data sampling time, i.e., 10 slice-encodings for 16 slices, and the data were zerofilled and reconstructed using the reconstruction program supplied by the manufacturer. On completing data acquisition of each echotrain, all imaging gradients can be completely rewound to preserve the transverse coherence and maintain some level of steady-state transverse magnetization.

Figure 2:
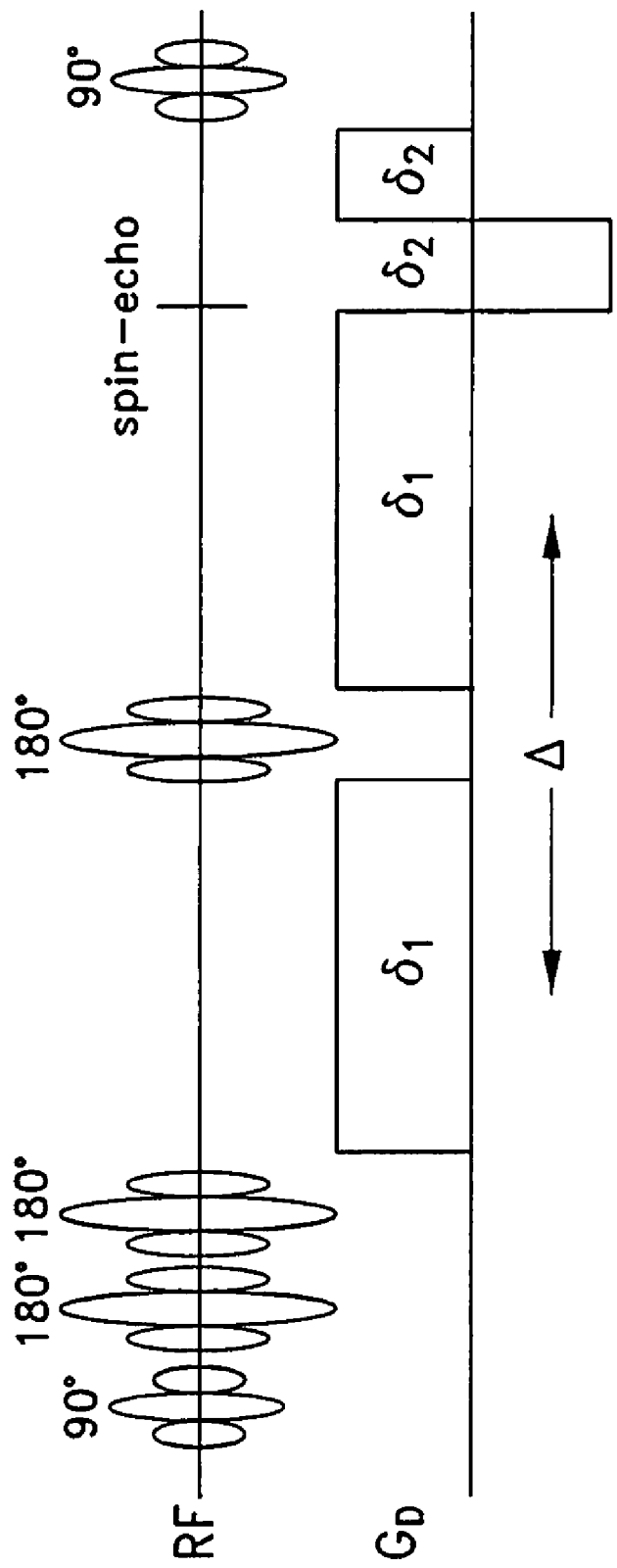
FIG. 2 depicts diffusion weighing in diffusion-prepared driven-equilibrium (DPDE) preparation.

FIG. 2 depicts a method of implementing diffusion weighing using 3D ss-DWSTEPI. The symbols δ and Δ represent the duration of diffusion gradient and the spacing between two main diffusion gradients, respectively. An extra delay is inserted between the DW spin-echo position and the 90° tipup RF pulse, which is same as the time interval between the center of the imaging RF pulse and the stimulated echo position. Diffusion weighting may be achieved by applying the Stejskal-Tanner diffusion-weighting gradient on both sides of the third 180° RF pulse (FIG. 1, section (a)) and additional bipolar gradients during the delay to maximize the diffusion weighting for a given TE. Neglecting gradient ramping up/down time, the b value for the diffusion weighting scheme can be given by:

$$b=(\gamma G_D)^2(\delta_1^2(\delta_1-\Delta/3)+\delta_2^3). \qquad (1)$$

Figure 3:
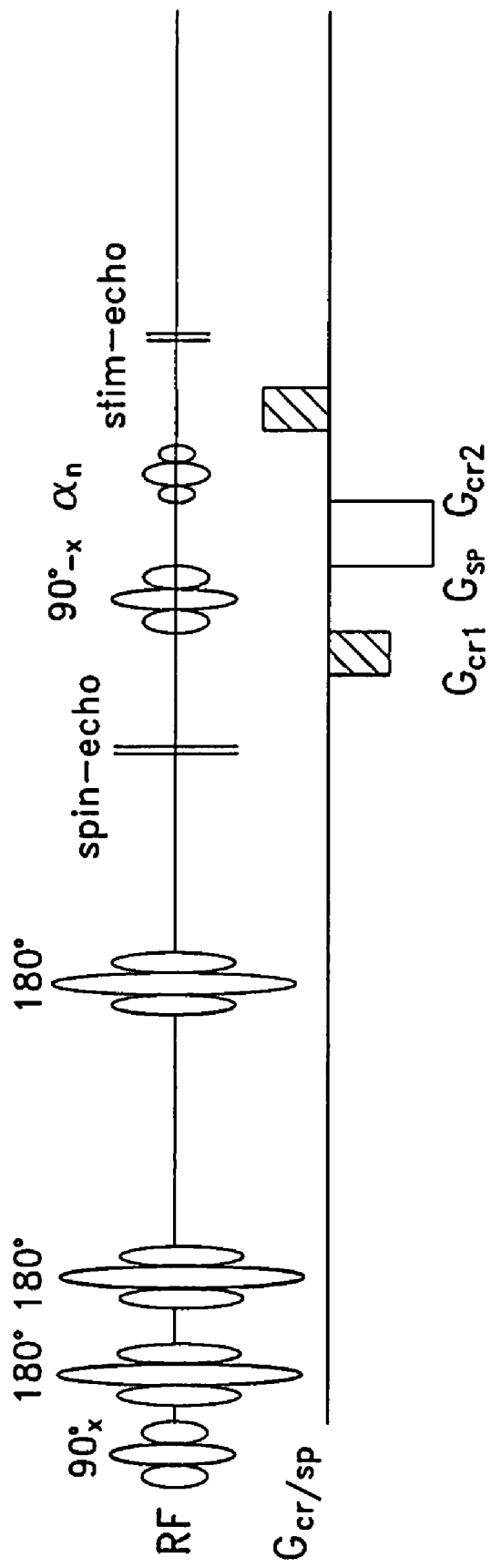
FIG. 3 depicts the formation of diffused weighted stimulated echo in DWSTEPI.

FIG. 3 describes the evolution of spins to form the diffusion encoded stimulated echoes in STEPI. DW magnetization $M_D^+(\vec{r})$ is refocused at the spin-echo position "SE". Then, $M_D^+(\vec{r})$ is dephased more than $2\pi$ by the gradient $G_{cr1}$ and the $90°_{-x}$ RF pulse tips half of the dephased magnetization to the longitudinal direction, leaving the other half in the transverse plane. The transverse component is spoiled by the spoiler gradient $G_{sp}$. As a result the DP magnetization with dephasing is aligned to the longitudinal direction before the imaging RF. The imaging RF $\alpha_n$ tips a fraction of the magnetization into the transverse plane, the crusher gradient $G_{cr2}$ rephases the dephasing caused by crusher gradient $G_{cr1}$, and a stimulated echo is formed at the position "STE", at the position where $k_y=0$ in the EPI readout.

Eq. (2) describes the longitudinal magnetization just before the $n^{th}$ imaging RF pulse with respect to the previous longitudinal magnetization value $M^z_{n-1}$. Here, $\alpha_n$ is the flip angle of the $n^{th}$ imaging RF pulse and $\tau$ is the duration of each data acquisition segment.

$$M_n^z(\vec{r})=M_o(\vec{r})(1-e^{-\tau/T_1(\vec{r})})+M_{n-1}^z(\vec{r},t_{n-1})\cdot\cos\alpha_{n-1}\cdot e^{-\tau/T_1(\vec{r})} \qquad (2)$$

The two terms in Eq. (2) are the freshly recovered and diffusion-prepared magnetization, respectively. A signal from the first term, which is not diffusion-weighted, is spoiled after each excitation by the rephasing crusher gradient (indicated by left arrow: ← in FIG. 1). As a result, the detected MR signal reflects only the diffusion-weighted magnetization, yielding a straightforward single exponential dependence on the applied b value. The diffusion-prepared longitudinal magnetization decreases along the slice-encoding direction due to the repeated RF pulses and $T_1$ decay.

Neglecting the steady-state transverse magnetization, the diffusion-weighted transverse magnetization after the $n^{th}$ imaging RF pulse $\alpha_n$ can be described as:

$$M_n^+(\vec{r}, TR, TE, b) = \qquad (3)$$

$$\frac{1}{2}M_D^z(\vec{r}, TR, TE, b)\cdot e^{-(n-1)\tau/T_1(\vec{r})}\cdot\sin\alpha_n\cdot\prod_j^{n-1}\cos\alpha_j,$$

where the diffusion-prepared magnetization is defined by:

$$M_D^z(\vec{r},TR,TE,b)=M_o(\vec{r})\cdot(1-e^{-(TR-T_{ACQ})/T_1(\vec{r})})\cdot e^{-bD(\vec{r})}\cdot e^{-TE/T_2(\vec{r})}\cdot e^{-TE/T_1(\vec{r})}, \qquad (4)$$

for diffusion weighting b, effective echo-time $TE=TE_1+TE_2$, a time delay, TD, between the tipup RF pulse and the first imaging RF pulse ($\alpha_1$), and total pulse sequence duration $T_{ACQ}$ which includes the diffusion-preparation and complete 3D data readout. The factor ½ arises from applying the pre-tipup dephasing gradient to remove the signal dependency on the relative phase between the tipup RF pulse and DW magnetization (20).

As shown by the second term in Eq. (2), the measured signals experiences $T_1$ rather than $T_2$ decay along the slice-encoding direction. This can be very advantageous, because $T_1$ is typically an order of magnitude longer than $T_2$ in most tissues. Blurring in the slice-encoding direction, which may arise from $T_1$ decay during the long data acquisition, may be reduced by using variable flip angles. The transverse magnetizations $M_{n-1}^+(\vec{r},t)$ and $M_n^+(\vec{r},t)$ after two consecutive RF pulses ($\alpha_{n-1}$ and $\alpha_n$) are:

$$M_{n-1}^+(\vec{r},t)=M_{n-1}^z(\vec{r},t_{n-1}^-)\cdot\sin\alpha_{n-1}$$

$$M_n^+(\vec{r},t)=M_{n-1}^z(\vec{r},t_{n-1}^-)\cdot\cos\alpha_{n-1}\cdot e^{-\tau/T_1(\vec{r})}\cdot\sin\alpha_n. \qquad (5)$$

To achieve equal signal amplitude ($M_n^+(\vec{r},t)=M_{n-1}^+(\vec{r},t)$) the relationship between the flip angles of two adjacent RF pulses should satisfy $$\tan\alpha_{n-1}=\sin\alpha_n\cdot e^{-\tau/T_1(\vec{r})} \qquad (6)$$

The flip-angle for the last RF pulse is set to 90° to consume substantially all remaining longitudinal magnetization, and the flip angles of the proceeding RF pulses can be calculated using the relation in Eq. (6), and typical values of τ and $T_1$ which are about 40 ms for 31 ETL with the receiver bandwidth of about 1.086 kHz/pixel and $T_1=1.0$ s (approximately) for white matter at 3T. In general, the use of this equation resulted in very small initial flip angles and, correspondingly, low SNR images. For this reason a compromise was made between $T_1$ decay related blurring in the slice encoding direction and image SNR, using a ramped variable flipangle with a larger starting angle and smaller increases, ending again in a 90° pulse to consume substantially all remaining longitudinal magnetization.

After completion of each EPI echotrain, the remaining transverse magnetization can be rewound or completely spoiled by a spoiler gradient. Because the central planes of k-space are acquired during the first few stimulated echoes, with rewinding or with spoiling the DWI signal intensity undergoes simple exponential decay with respect to the b value, as:

$$M^+(\vec{r},TE,b)=M^+(\vec{r},TE=0,b=0)\cdot e^{-TE/T_2(\vec{r})}\cdot e^{-b\cdot D(\vec{r})}. \qquad (7)$$

Figure 4:
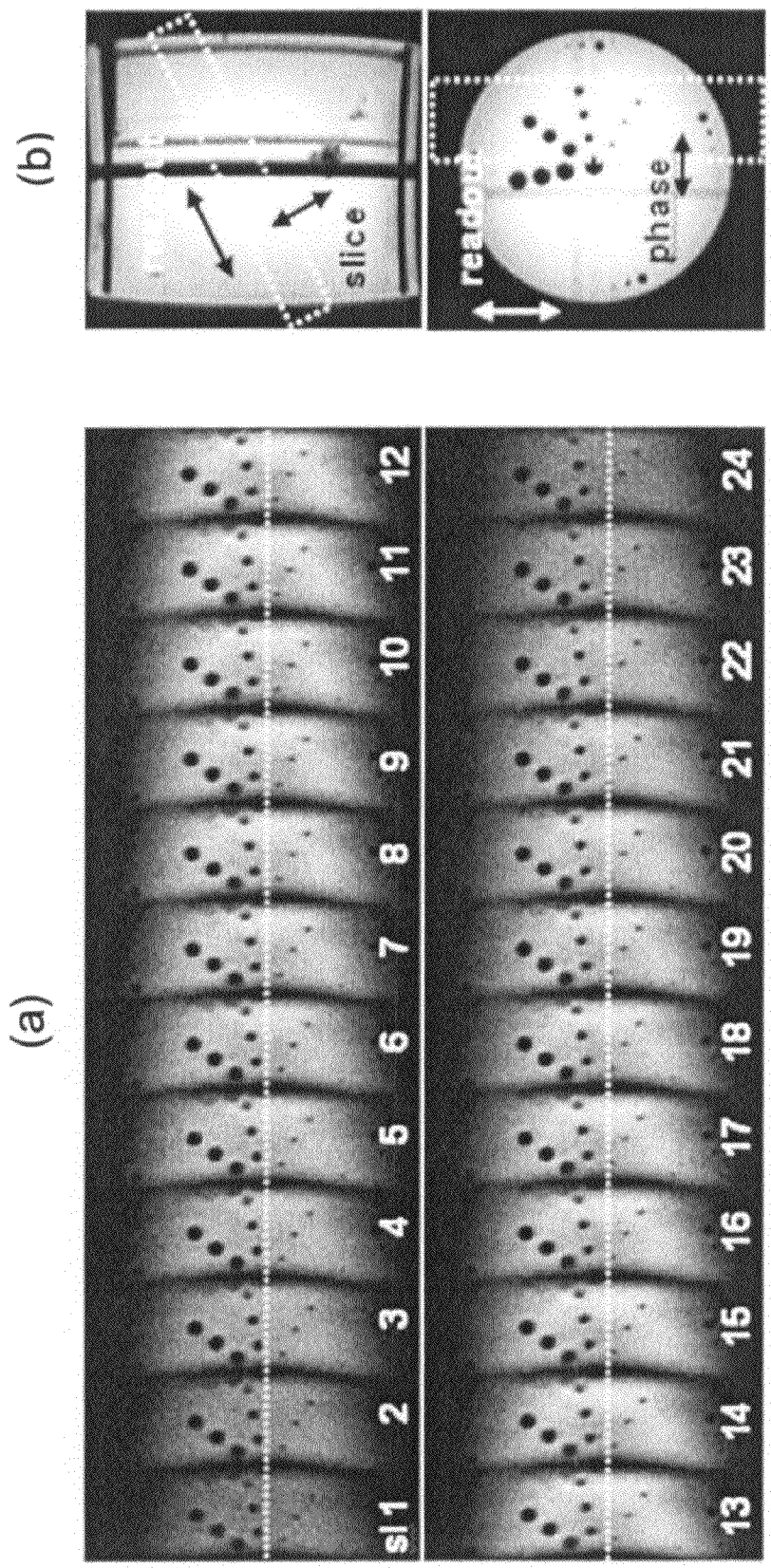
FIG. 4 depicts diffusion-weighted images acquired by 3D ss-DWSTEPI.

FIG. 4 depicts images obtained by 3D ss-DWSTEPI for reduced phase FOV preparation. The prescribed volume is indicated by the dotted box in section (b). The resulting images have a good quality without any aliasing along the phase-encoding direction from the phantom regions external to the prescribed volume. This result demonstrates the applicability of our reduced FOV preparation scheme to limit FOV in the phase-encoding direction. Such a restricted in-plane FOV can be sampled by a short EPI readout resulting in significantly reduced image distortion due to local magnetic field susceptibility. The degree of distortion in the images acquired by 3D ss-DWSTEPI was comparable to that of 2D ss-DWEPI with analogous EPI readout duration. Note that the 3D ss-DWSTEPI data acquisition was accomplished with 15 applications of the excitation RF pulse followed by the EPI acquisition of 31 gradient echoes. The duration of each segment including the RF pulse and complete $k_y$ acquisition of 31 gradient echoes was about 38 ms. The total duration of the 3D data acquisition was around 560 ms for the 15 actual slice-encodings required to reconstruct a 24-slice volume.

In certain embodiments, 2D STEPI has been tested and given MR images with greatly reduced geometric distortion. It may be an important tool for a high-field MRI system, such as a system where b of equation 7 is greater than or equal to 3T. In 3D STEPI, kz (slice) encoding may be segmented along a stimulated echo train, and each segment can complete the entire $k_y$ (phase)-encoding. In 2D, the total $k_y$ is interleavely segmented into multiple stimulated-echotrains. The geometric distortion of the resultant MR images is 1/(Number of segments) of that of conventional 2D singleshot-EPI.

Figure 5:
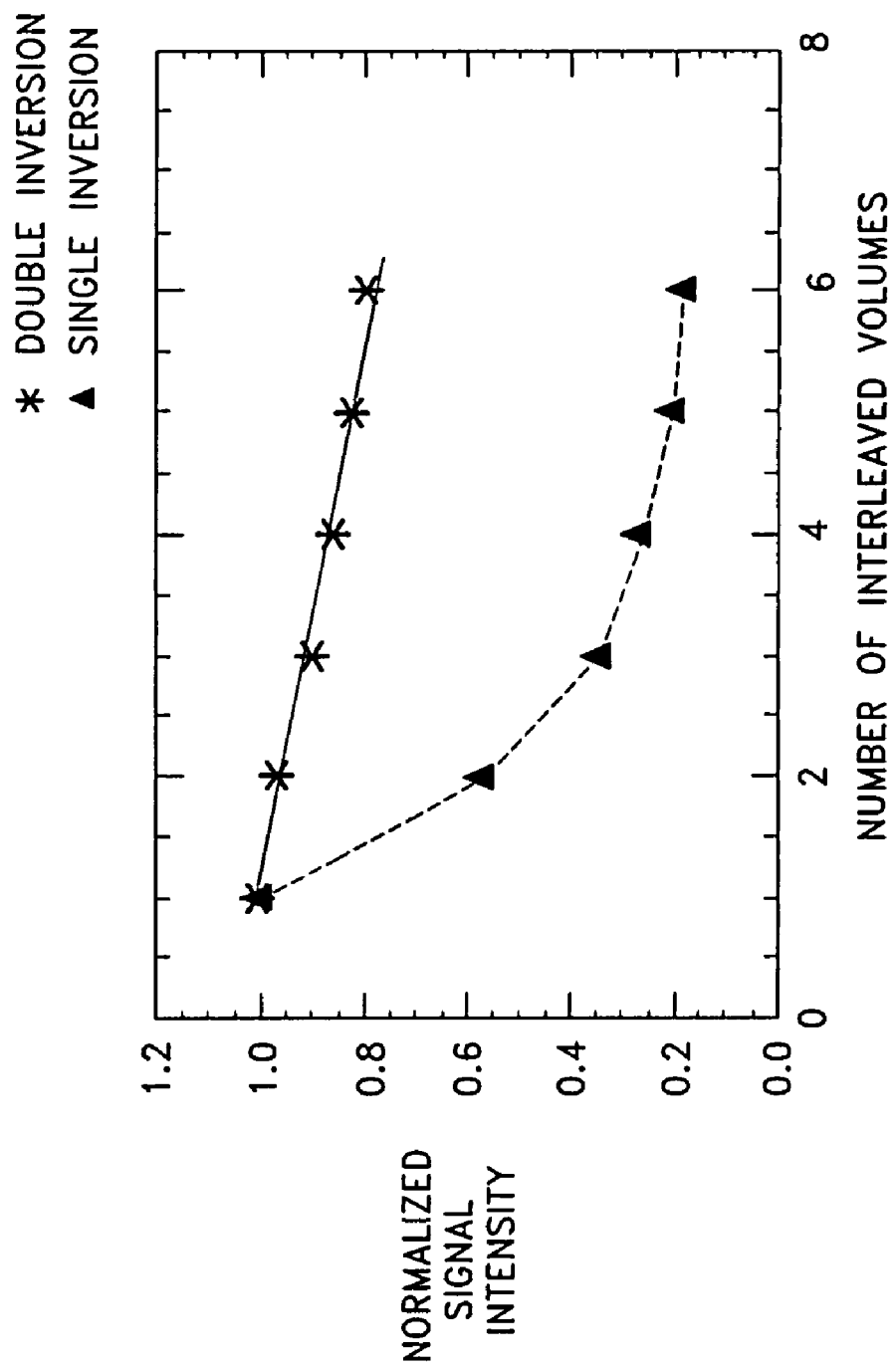
FIG. 5 is a graph depicting signal intensity for single and double inversion preparation.

As shown in FIG. 5, the signal loss in interleaved multislab imaging with reduced FOV preparation was substantially reduced using the new technique with double inversion (□) compared to the rapid signal decay for the standard method with a single inversion pulse (Δ). Adiabatic RF pulses with about 5.12 ms duration were used to implemented double inversion reduced FOV preparation. The separation between the inversion RF pulses in the new technique was around 6.0 ms.

Figure 6:
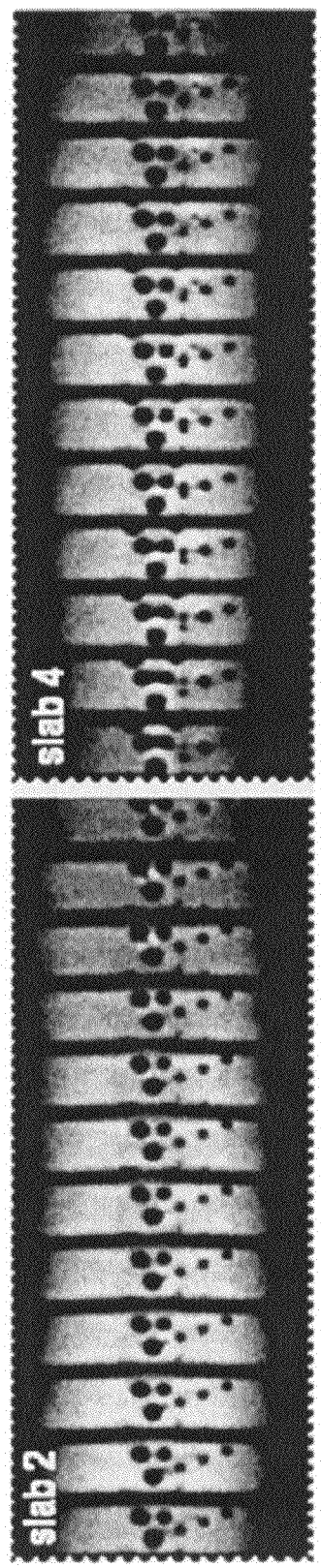
FIG. 6 depicts diffusion-weighted images of multi-slab 3D ss-DWSTEPI.

FIG. 6 illustrates two sets of 12 slices from 4 contiguous 12-slice slabs. Two separate acquisitions (passes) were used to image slabs 1 and 3 in the first acquisition, and slabs 2 and 4 for the second. The signal loss evident on the edge slices of each slab is due to the RF profile variation and is a common problem in most 3D imaging methods.

Figure 7:
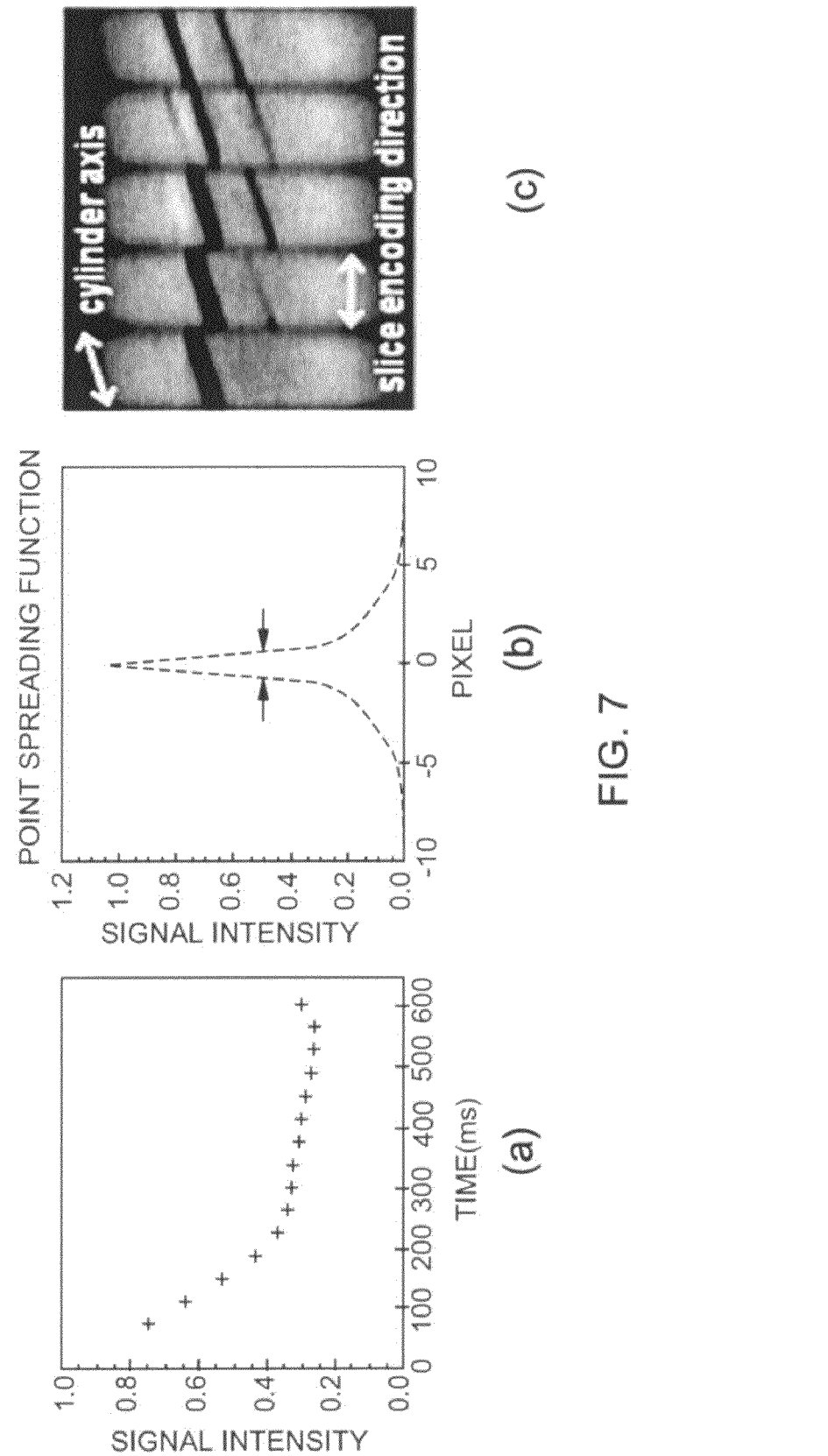
FIG. 7 depicts affects of decreasing the number of slice-encodings.

FIG. 7 depicts the affects of decreasing the number of slice-encodings. More particularly, by reducing the number of slice-encodings, the blurring in the slice direction can be reduced. Blurring can also be improved by using a small starting flipangle with an increased number of averages to obtain acceptable SNR. The peak amplitudes of the stimulated echoes are plotted section (a), with respect to their occurrences in time relative to the excitation RF (t=0) in DPDE. The amplitude of the later echoes of 3D data readout was about 40%, compared to the first echo ($k_z$=0). The corresponding point-spread-function (PSF) is shown in section (b). The full width at half of maximum for the PSF was about 1.8 pixels indicating that image blurring in the slice direction was mild. The 3D interleaved multiple inner volume ss-DW-STEPI images shown in FIG. 4 (xy-plane) and section (c) of FIG. 7 (xz-plane) demonstrate high resolution without any noticeable blurring in the slice encoding direction.

The image distortion observed in STEPI is a function of the number of echoes in the EPI echotrain. Because there are typically more phase encodings than slice encodings, the number of echoes in the EPI echotrain can be reduced by interchanging phase and slice encoding. With this switch, slice encoding is performed in conjunction with the EPI readout and one phase encoding is applied for each EPI segment.

Figure 8:
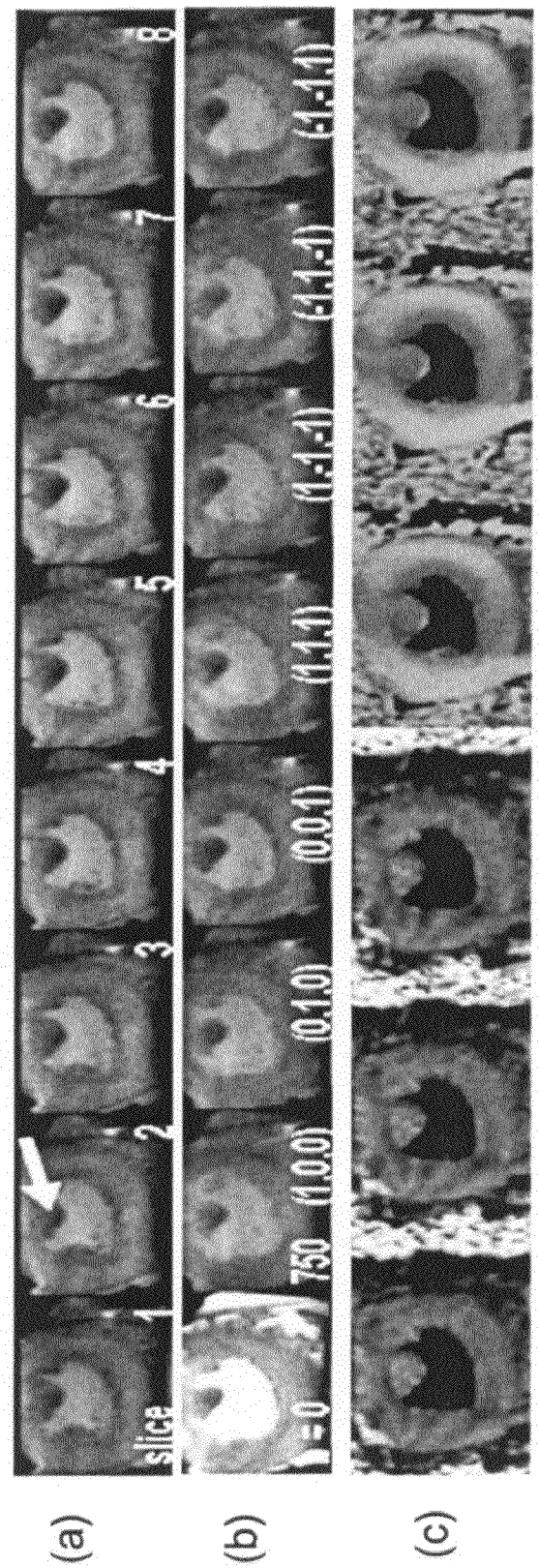
FIG. 8 depicts diffusion-weighted images of a fresh excised canine heart.

The results of a DTI study of a canine heart ex vivo are shown in FIG. 8. There are some residual aliasing artifacts at the left portions of the images along the phase-encoding direction. The helical structure of the myocardial muscle is well presented in the color map, similar to results previously reported from the excised animal hearts.

Figure 9:
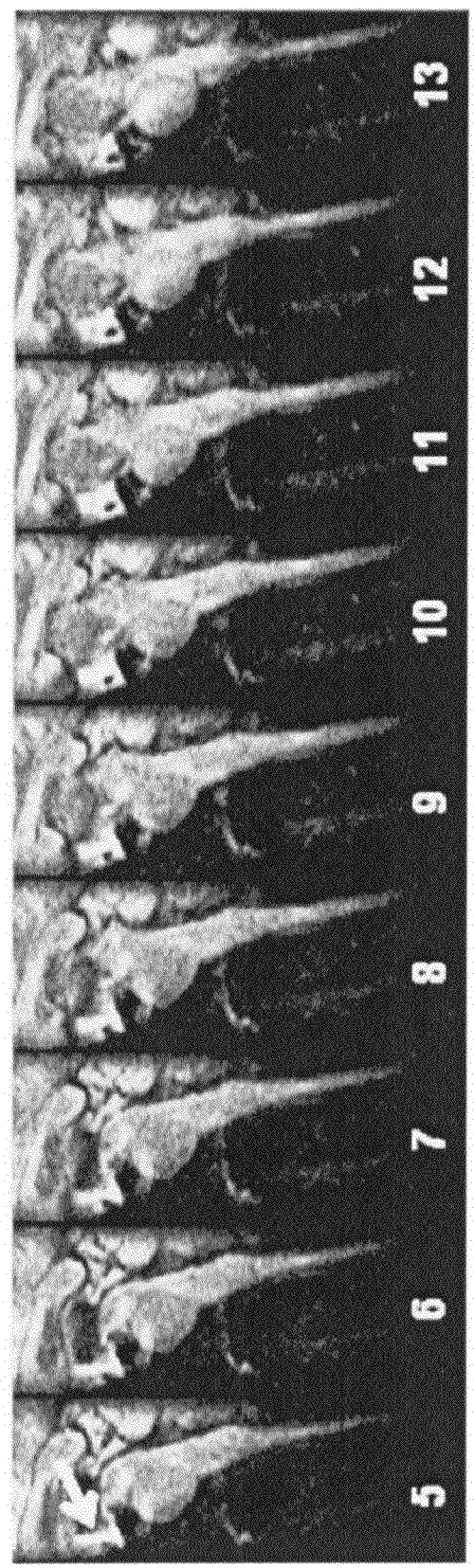
FIG. 9 depicts diffusion-weighted images acquired by 3D ss-DWSTEPI.
Figure 10:
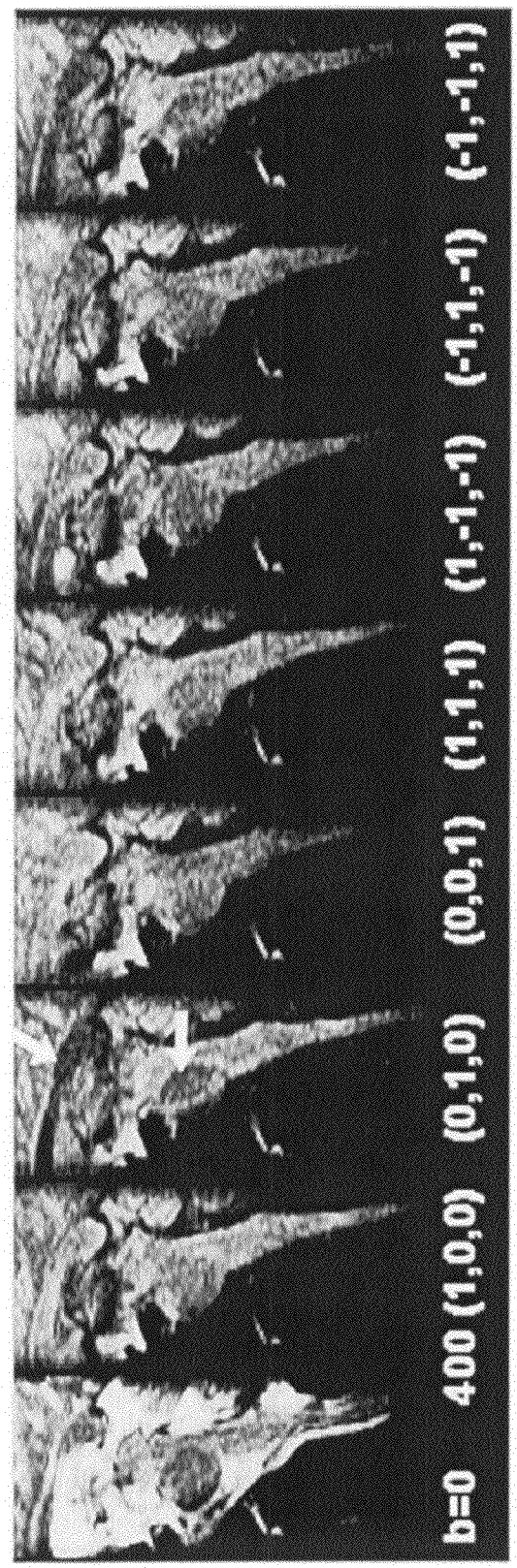
FIG. 10 depicts diffusion-weighted images of a slice.
Figure 11:
FIG. 11 depicts DTI measurements of a healthy human midbrain and principal eigenvector maps.

The images from a DTI study of the midbrain of a healthy volunteer are presented in FIGS. 9-11. Note that the images were acquired using a head coil, in which the signal reception sensitivity rapidly drops near the mid level of cervical spinal cord. FIG. 9 shows 9 central slices from 16 contiguous slices covering an approximately 20 mm thick slab. The bright signal indicated by the arrow appears to be a susceptibility induced artifact.

DW images of the central slice are shown in FIG. 10 for b=0 s/mm$^2$ and about 400 s/mm$^2$ for 7 non-collinear directions. DW images were processed to estimate DTI parameters, such as eigenvectors, eigenvalues, and fractional anisotropy (FA). The resultant FA maps and RGB colored maps of the principal eigenvector are presented in FIG. 11 for the central 9 slices, which completely cover the cervical spinal cord in the transverse direction. These results are very promising for in-vivo human applications of 3D ss-DWSTEPI for high-resolution DTI.

3D ss-DWSTEPI can acquire the diffusion-weighted magnetization of a localized volume after a single diffusion preparation. Even though spatial coverage is limited in the phase and slice directions, the FOV in the readout direction can be arbitrary and limited by the desired image dimensions and the sensitivity volume of the receiver coils. The system and method described herein not only reduces susceptibility artifacts by using significantly shortened EPI readouts, but also freezes most of the physiologic motion by using a single short data acquisition. 3D ss-DWSTEPI can be useful for high resolution 3D DTI of limited volumes of interest such a localized brain regions, cervical spinal cord, optic nerve, heart or other extracranial organs.

Motion Artifact Correction in 3D Multishot EPI-DTI with Real-Time 2D Navigators

Subject motion during the diffusion gradients can cause shading and ghosting artifacts in the resultant diffusion-weighted (DW) images [1-3], and consequently result in reduction of the accuracy of DTI measurement in multishot DW imaging. Typically, DW images are acquired with multiple signal averages to improve SNR. Any discrepancy in subject position between averages would result in blurring of the averaged image. We hypothesized that any motion might decrease the accuracy of DTI measurement in multishot or multiple averaging singleshot DTI. In this report, a motion artifact correction scheme for multi-shot 3D EPI-DTI with one EPI readout per kx-ky or kx-kz plane is described. This technique can be used to reduce artifacts caused by subject motion during diffusion gradients or subject motion between shots or averages and, therefore, to improve the accuracy of DTI measurement.

Figure 12:
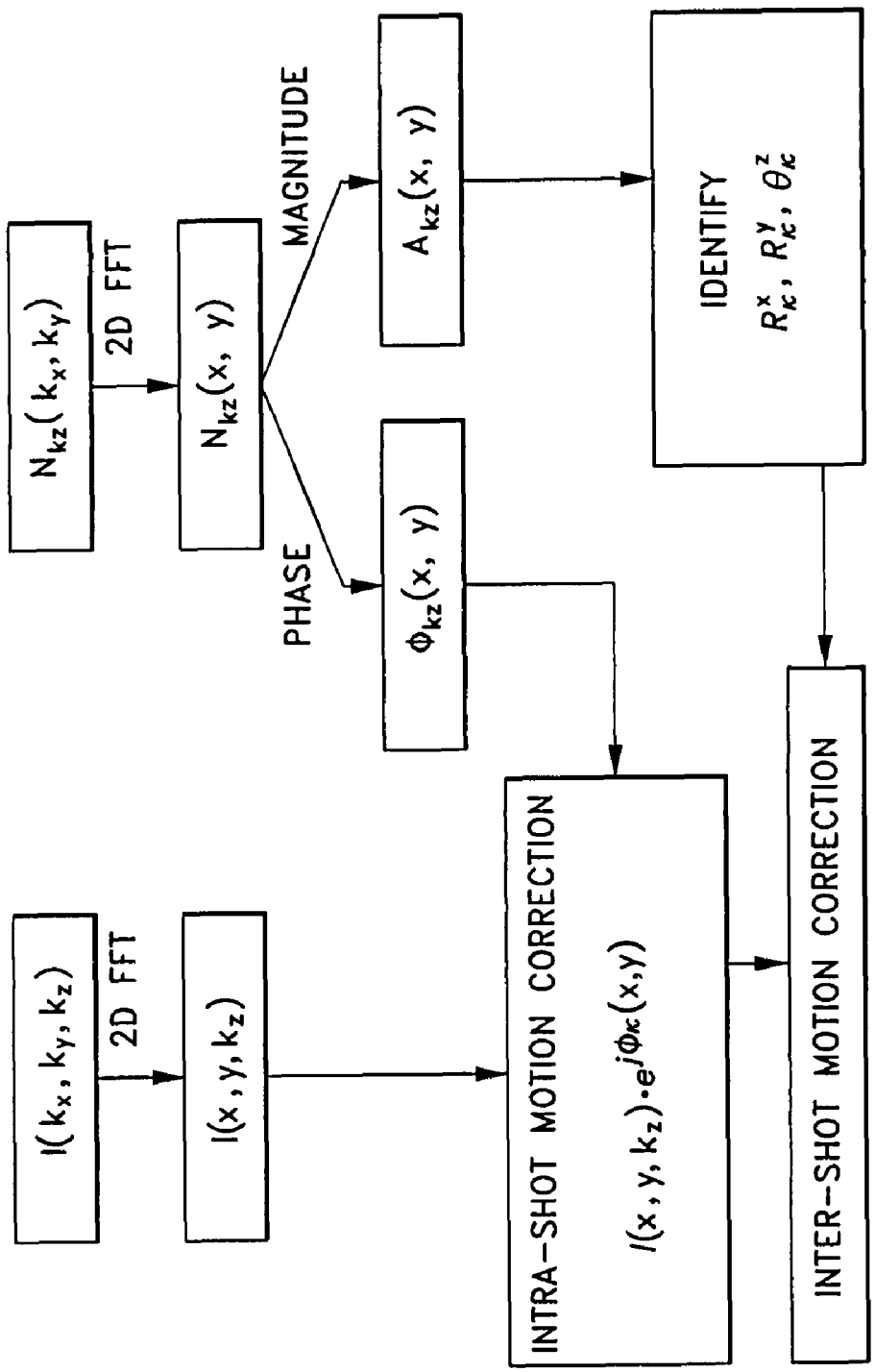
FIG. 12 illustrates one embodiment for a motion artifact correction scheme for multi-shot 3D EPI-DTI with one shot per kx-ky plane.

Data acquired by multi-shot DTI pulse sequences can be corrupted by two principal types of motion: motion during diffusion gradient application (intra-shot motion) and motion between shots (inter-shot motion). Intra-shot motion can cause a significant signal loss when even small motion can cause partial or complete dephasing or an additional phase factor in image space. Inter-shot motion caused by global changes in subject position results in additional phase term in k-space data (translation) or k-space data shift (rotation). Both types of motion can be identified and corrected if multi-dimensional navigators are acquired together with the imaging data. A 3D multi-shot EPI-DTI pulse sequence with a limited FOV preparation and 2D navigators was implemented. In the sequence, two techniques were used to resolve the motion: (1) real time (RT) navigation of data acquisition and (2) correction of inconsistencies between shots using 2D navigators. The first technique, RT navigation, can be used to monitor/identify the shots corrupted by substantial motion, and direct the pulse sequence to reacquire data for those shots. The second method can identify and remove inconsistencies caused by small motions between shots and can identify and correct the resulting subject position changes. The method for motion artifact correction in 3D multi-shot DTI with 2D navigator echoes is schematically described in FIG. 12.

The input data is the measurement data with strongly motion corrupted shots reacquired. Combination of image data with the 2D navigator phase is used to suppress motion artifacts. Parameters $R_{kz}^x$, $R_{kz}^y$, $\theta_{kz}^z$ describe inter-shot translation and rotation.

The input data for the technique are the dataset with excessive motion corrupted echoes reacquired in real-time. The measurement data were obtained using 3D multi-shot EPI-DTI pulse sequence with limited FOV preparation. The imaging parameters were: b=500 sec/mm$^2$, TR/TE=4000/75 ms, ETL 33, 192×33×8 imaging matrix, and 4 averages. The first average was treated as the acquired data, while the remaining 3 averages were considered as the reacquired data to simulate RT navigation. The agar phantom was intermittently moved predominantly in the vertical or horizontal direction during the acquisition to mimic physiologic motion. The algorithm described in FIG. 12 was used to correct the phase inconsistency between shots. First, 2D navigator echoes $N_{kz}(k_x,k_y)$ were Fourier transformed and the corresponding 2D phase maps $\phi_{kz}(x,y)$ were constructed. These maps were combined with the associated imaging echoes as $I'(x, y, k_z)=I(x, y, k_z)e^{i\phi_{kz}(x,y)}$ [1]. Inter-shot in-plane motion (translations ($R_{kz}^x$, $R_{kz}^y$) and rotation ($\theta_{kz}$) in x-y plane) can be estimated from the 2D navigator image, $A_{kz}(x,y)$ using the methods described in [3]. The corrected dataset was used for image reconstruction.

Figure 13:
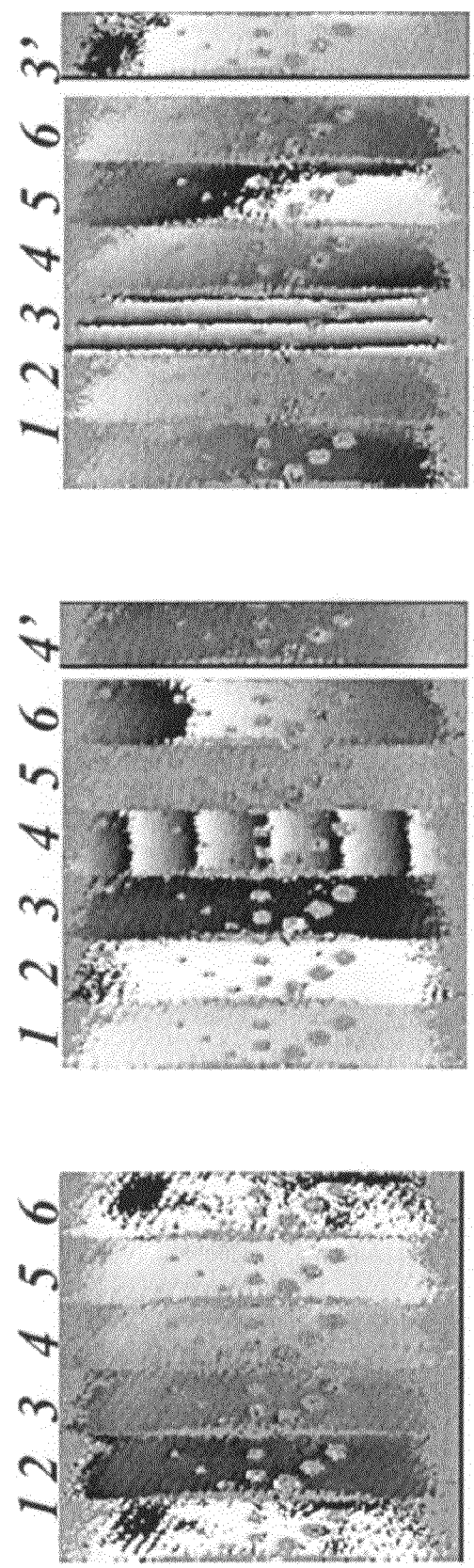
FIG. 13 illustrates a simulation of RT navigation phase maps of the 2D navigator echoes of an agar phantom with $b=500$ s/mm$^2$.

FIG. 13 illustrates the real-time reacquisition of the imaging echoes corrupted by excessive motion. Numbers on top of the figure represent shot number and the numbers with prime (4' and 3') represent the reacquired shot. The phantom was (a) stationary or intermittently moved/rotated during the acquisition mainly in (b) vertical or (c) horizontal direction. The RT navigation directed the pulse sequence to reacquire the motion-corrupted echoes. The shot where the peak of the associated 2D navigator k-space data is shifted noticeably were replaced by the corresponding shot from next average (RT navigation). The resulting dataset was used for the phase-correction.

Figure 14:
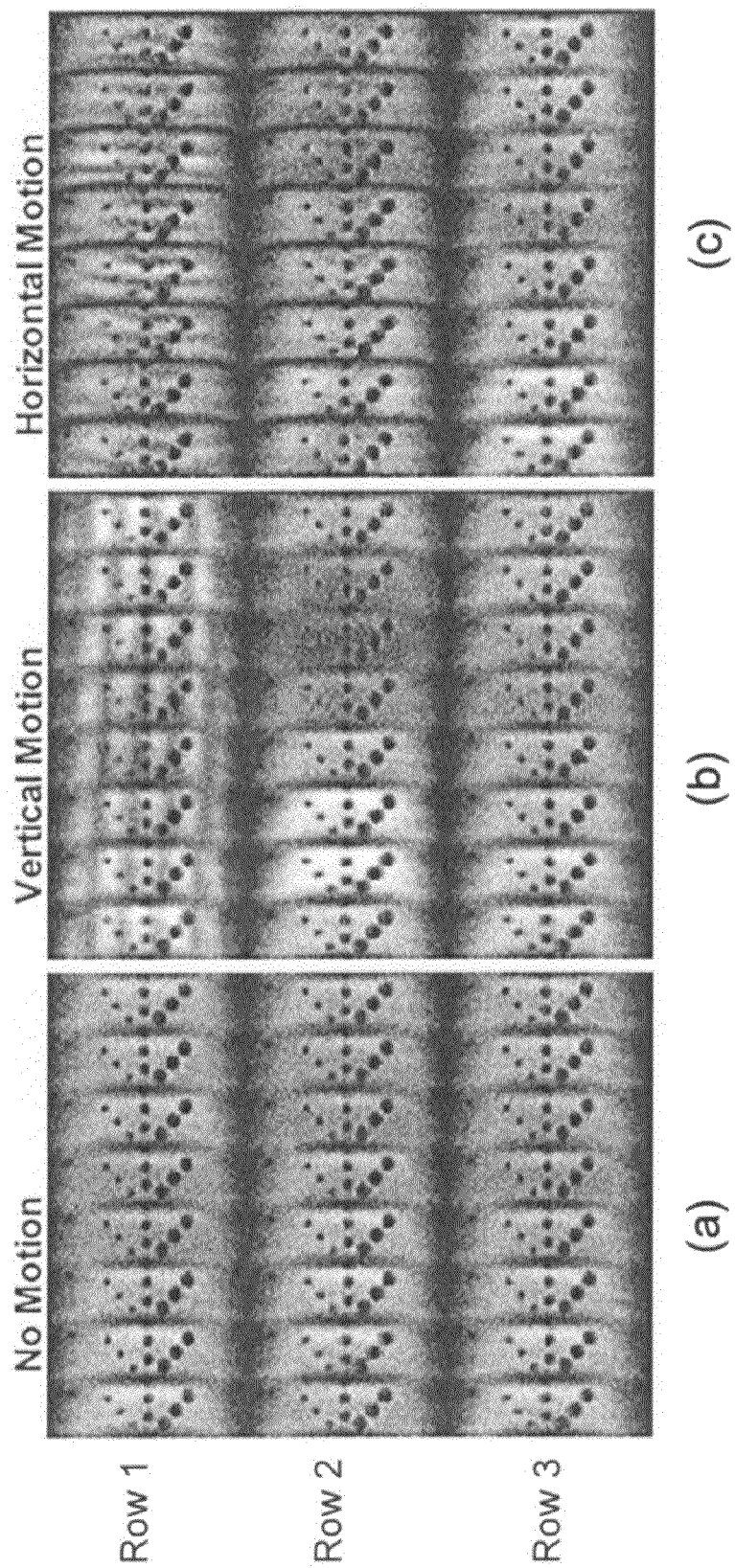
FIG. 14 illustrates 3D DW images of 8 contiguous slices obtained with $b=500$ sec/mM$^2$ along the S/I direction (in/out-of the image plane).

FIG. 14 shows the images reconstructed from the original dataset (row 1), the dataset after RT navigation (row 2), and the dataset after phase inconsistency correction (row 3). The images from row 1 in column b and c are corrupted by motion artifact. The reacquisition of data by RT navigation improves image quality significantly (row 2 of FIG. 14) but leaves some residual ghosting in the slice direction, especially in images corrupted by vertical motion. These residual artifacts are removed after phase correction (row 3 of FIG. 14). The horizontal banding in all images is a systematic artifact arising from the shape of the RF profile used for reduced FOV preparation and does not affect the DTI processing as it presents in all images.

With reference to FIG. 14, the phantom was stationary or intermittently moved vertically or horizontally during data acquisition. The DW images in the second row were reconstructed from the dataset where the motion corrupted EPI readouts were replaced by the corresponding readouts from next average dataset (simulation of RT navigation). The dataset after RT navigation was additionally corrected using 2D navigator phase information. The phase correction combining with the RT navigation gave substantially improved DW images.

In some embodiments, a new imaging technique, 2D singleshot Real-Time Navigated diffusion-weighted EPI (2D ss-RTN-DWEPI), is used to acquire DWI, which the data is monitored in real-time by using the real-time feedback capability of the MRI system, to identify the data with substantial corruption due to the motion. The largest echo peak of 2D navigator echoes is searched and its magnitude and the position calculated for evaluation of RTN test by comparing the later averages to the first average of the same diffusion encoding in real-time. If the differences are out of bound from the given threshold, the data is rejected and immediately reacquired in real-time.

The RTN data acquisition is implemented into 2D ss-EPI, using the IDEA pulse sequence development environment, and the real-time calculation of the navigator data is implemented into an image construction program in Image Construction Environment (ICE) (Siemens Medical Solutions, Erlangen, Germany). The pulse sequence (FIG. 15) is capable of Interleaved Multi-slice Inner Volume imaging (IMIV) of a reduced field-of-view (FOV) without the aliasing artifact in phase-encoding direction, using the application of the double inversion immediately after the 90° excitation RF. An adiabatic RF pulse is used for double inversion for IMIV. The first inversion RF does not accompany the slice-selection gradient and the second with slice-selection gradient in phase-encoding direction that defines the reduced FOV phase-encoding direction. The application of double inversion increases TE by about 12 ms, which includes two 5.12 ms RF pulses and two pairs of crusher gradients, sandwiching around the RF pulse to destroy the free-induction-decay caused by imperfect 180° pulse which generally induces the stimulated echo artifact.

Diffusion weighting is accomplished by adding a pair of Stejskal-Tanner diffusion-weighting gradient on both sides of the refocusing 180° RF pulse (the third 180° RF in the diagram). Real-time feedback flag (RT_FEEDBACK) is added to all EP imaging echoes. Therefore, the acquired data serves as the 2D navigator echoes as well as the imaging echoes. Upon the transfer of the raw data to the image construction computer, the echo data with the flag RT_FEEDBACK is immediately fed into the real-time calculation algorithm, which searches for the largest echo in k-space and calculated its coordinate $k_{pk}$ and magnitude $m(k_{pk})$ and sends these values to the scanning computer for the RTN test. The location $k_{pk}$ of the largest peak of the 2D echoes corresponds to the center of k-space. Images are constructed for the shots, on which the RTN test is passed.

Figure 15:
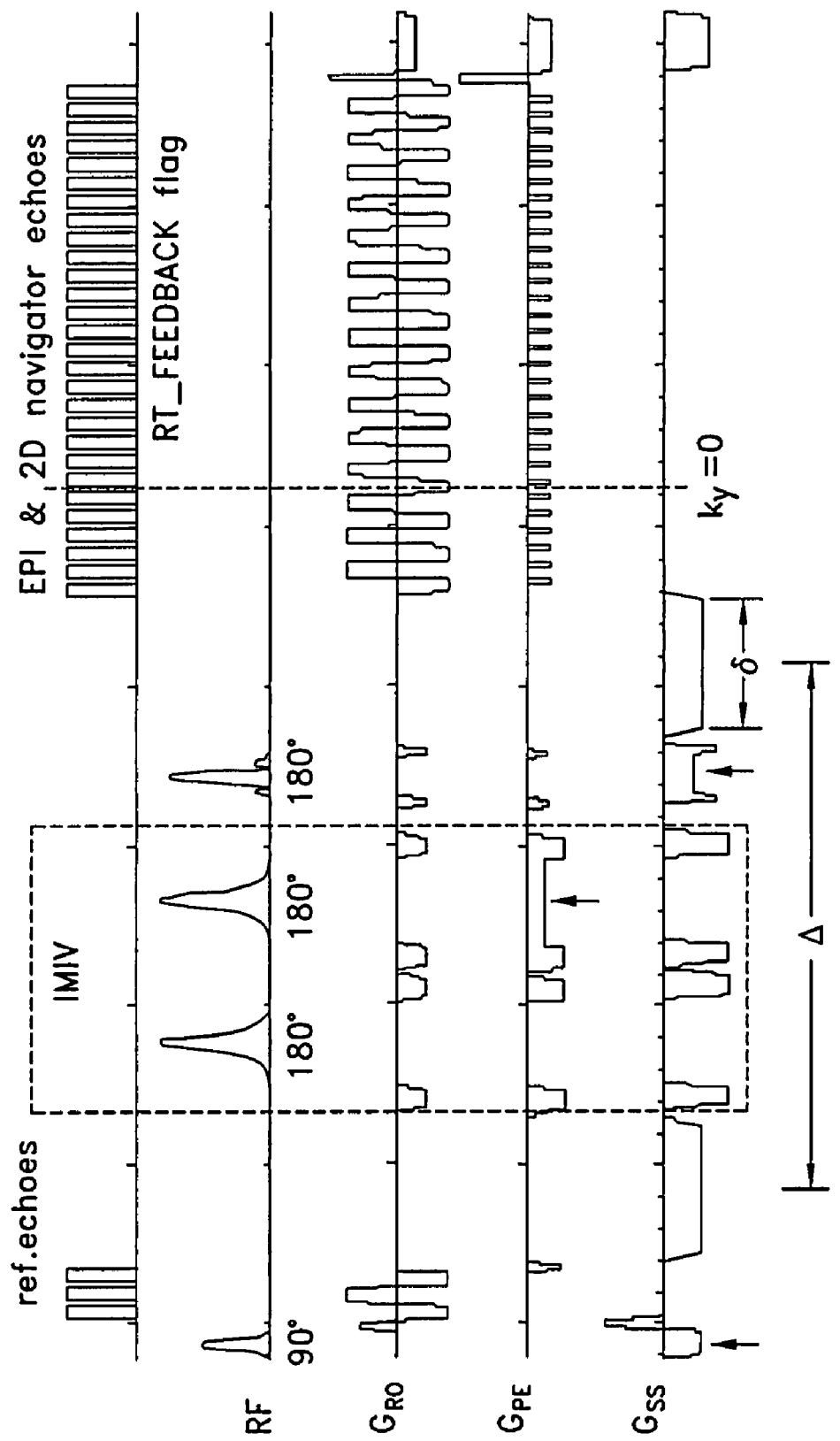
FIG. 15 depicts a 2D ss-RTN-DWEPI pulse sequence.

FIG. 15 illustrates a pulse sequence diagram of 2D ss-RTN-DWEPI with interleaved multislice inner volume imaging. Vertical arrows indicate the slice-selection gradients. Two 180° RF pulse enclosed within the dotted box are for reduced FOV imaging in phase-encoding direction. Slice selection gradient is applied in phase-encoding direction to restrict the imaging FOV. EP echoes were also set for RT_FEEDBACK flag for the real-time calculation. The dashed vertical line indicates the position of spin-echo and the center of k, i.e., k=0.

One may assume that a human subject is generally motivated to hold still at the earlier acquisition of imaging than the later ones. The first averaging data for all diffusion encoding directions are acquired at the early acquisition by using the long-term average mode, which the averaging resides at the outermost loop of the data acquisition. The first average data of each diffusion encoding direction was then considered as the reference shot without motion corruption. The scanning computer stores the reference values (m($k_{pk}$; $k_{pk}$) of the first averages to compare those of the later shots to monitor the change of the magnitude and the position of the largest echo in k-space and to determine if the data are acceptable.

Figure 16:
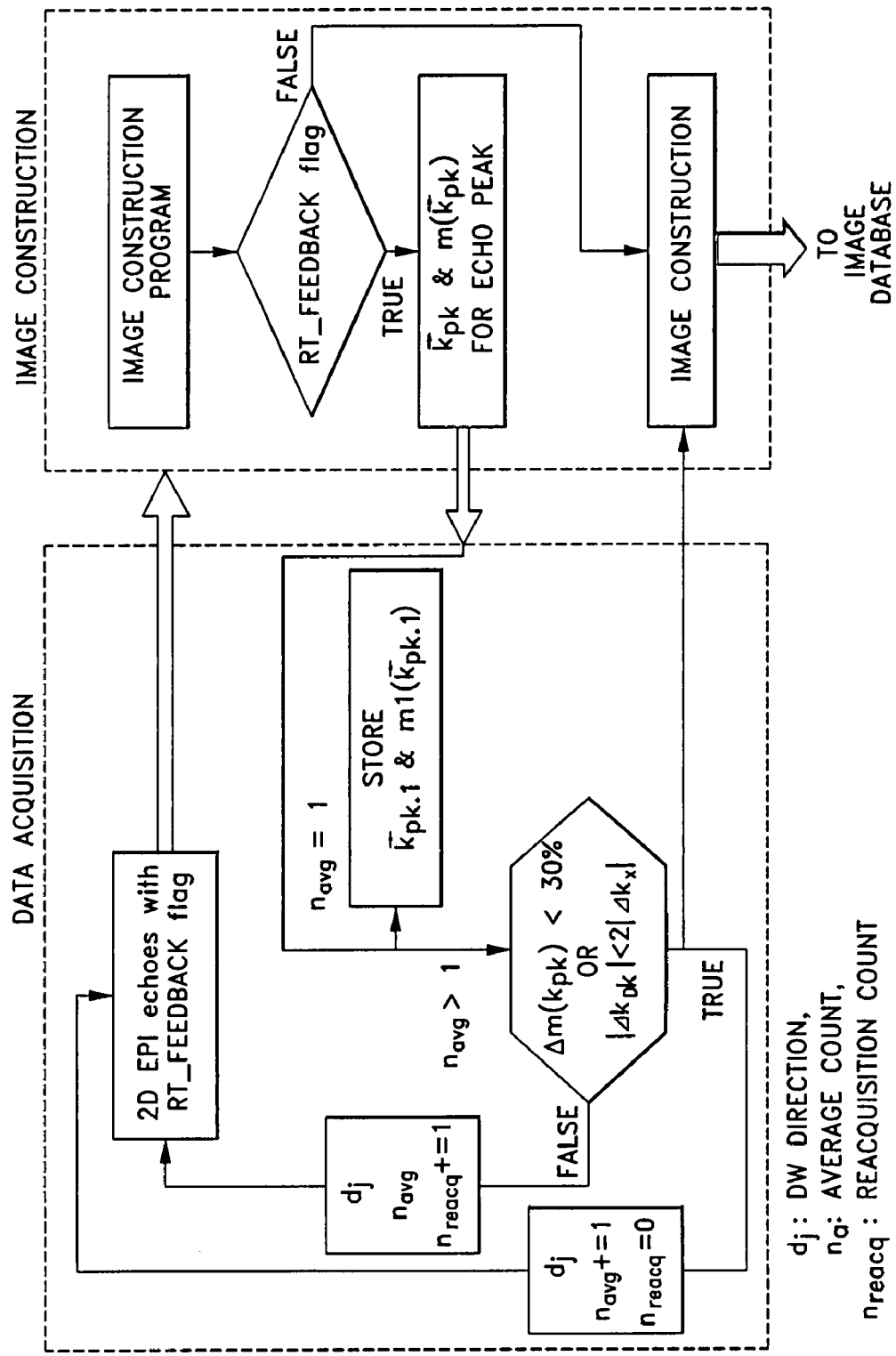
FIG. 16 depicts a flowchart of RT navigated acquisition and real-time calculation of specific diffusion encoding $d_j$.

The flowchart shown in FIG. 16 describes the RTN procedure of 2D ss-RTN-DWEPI. The dashed and the dotted boxes indicate the processes in the image acquisition and the image construction computers. The real-time calculation is processed by ICE program within the image construction computer. Indices $n_a$, $n_{reacq}$, and $d_j$ indicate average, reacquisition, and diffusion encoding counts, respectively. The position $k_{pk,1}$, and the magnitude $m_1(k_{pk,1})$, of the largest echo in 2D navigator echoes of the first averaging shot ($n_a$=1) are stored into a temporary memory as the reference values and are used for the comparison for other averaging data. For a specific diffusion encoding direction $d_j$ and averaging count $n_a$, the maximum reacquisition is set to avoid the extended acquisition duration. If the data successfully pass the RTN test or the reacquisition count reaches the maximum, the reacquisition count $n_{reacq}$ is reset to zero, which also directs the image construction computer to construct the images and send them to the image database. The averaging proceeds to the next acquisition.

In FIG. 16 thick arrows represent the data transfer between the acquisition and the reconstruction computers. All NMR data which is also 2D navigator echoes are sent to the reconstruction computer to search for the largest echo peak and to calculate its magnitude and the position in k-space. These values are transferred to the scan computer to determine if the data is acceptable compared to the first repetition data.

MR Imaging.

By way of example, MRI studies were performed on a Siemens Trio 3 Tesla MRI system (Tim Trio, Siemens Medical Solutions, Erlangen, Germany) with Sonata gradients (40 mT/m strength and 150 T/m/s slew rate).

Imaging Phantom: A cylindrical phantom filled with the mixture of water and agarose was used. $T_1$ of the phantom was measured about 2.0 s at 3 T. The phantom was intermittently lifted from one end or horizontally rotated during the acquisition. The imaging was accomplished using the parameters, the receiver bandwidth of 1.086 kHz/pixel and 31 actual echoes per EPI echotrain. A single channel transmit/receive RF coil was used for the simplicity of the raw data. Other parameters typically were that slice thickness was 2.0 mm, and TR/TE was 4.0 s/60 ms. The imaging matrix was 128×48 and 16 slices, with 62.5% asymmetric acquisitions in phase-encoding direction, which covered 96 mm and 32 mm in the phase and slice encoding directions for about 2.0 mm isotropic resolution. For the phantom imaging, 37.5% of full FOV was imaged in phase-encoding direction, using IMIV to image the reduced FOV without aliasing artifact. The averaging was accomplished via the magnitude averaging to remove the motion artifact. Otherwise the phase instability among the different averages may deteriorate the image quality.

A set of 2D ss-RTN-DWEPI images was acquired with diffusion weighting b=0 and 500 s/mm² in four non-collinear directions, (1,0,0), (0,0,1), (1,0,1), (−1,0,1) in physical gradient coordinate ($G_y$, $G_x$, $G_z$) that represent (vertical, horizontal, magnet bore) or anterior/posterior, right/left, superior/inferior (A/P, R/L, S/I) anatomic directions. The phantom was intermittently moved during the acquisition to simulate a subject's random physiological motion. The maximum number of reacquisition was set to 2 and the threshold values for RTN testing were 30% and 2$\Delta k_x$ for changes of the magnitude and the peak position. The minimum number of slices for the failure of RTN test was set to 2 for the interleaved multislice 2D imaging. For instance, if two or more slices out of total slices would fail RTN test, the acquisition of whole slices were repeated for that average that increased the total imaging time by an additional TR.

Human Imaging: To demonstrate the feasibility of the RTN for human imaging, 2D ss-RTN-DWEPI was applied to acquire DWI from human volunteers using image matrix 128×96 with an FOV of 256×192 mm, TR/TE 5.0 s/66 ms, b of 0 and 750 s/mm² in 7 non-collinear directions along three orthogonal axes and four tetrahedral vertices: (1,0,0), (0,1,0), (0,0,1), (1,1,1), (−1,−1,1), (1,−1,−1), (−1,1,−1). A twelve channel receive-only head-matrix coil (Siemens, Erlangen, Germany) was used. The channel within the posterior matrix was selected for RTN evaluation. During the data acquisition, subjects were instructed to move the head along anterior-posterior direction. Due to the narrow space in the headcoil, the subject's motion was mostly the rotational motion. DW imaging was repeated for the same volunteer without head motion. The subject was instructed to hold the head position, but with free breathing and swallowing. The imaging protocol was approved by the University of Utah Institutional Review Board and the informed consents were collected from volunteers.

Figure 17:
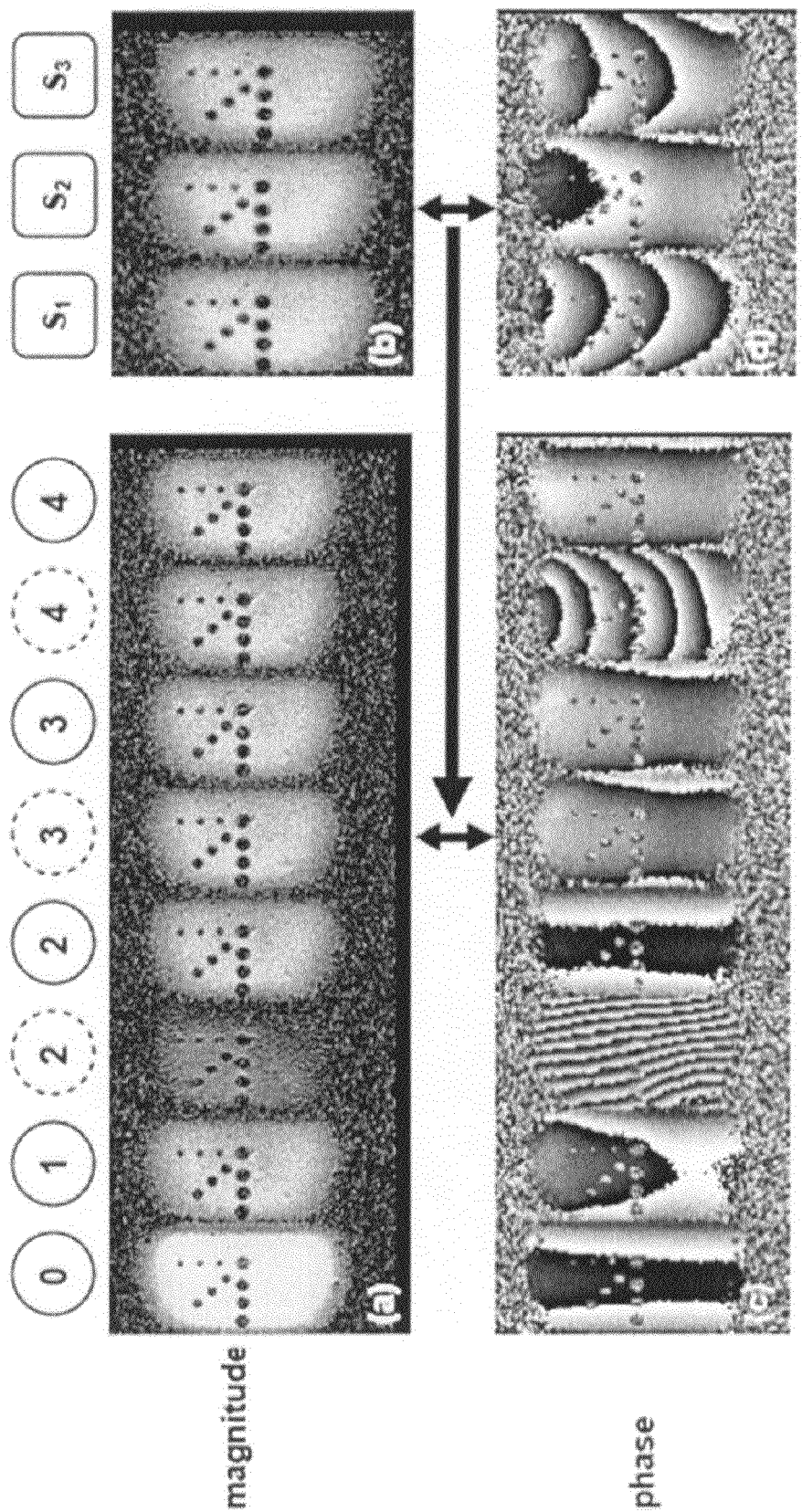
FIG. 17 shows motion corrupted magnitude and corresponding phase images of slice 7 in different diffusion encoding direction, compared with respect to motion free shot.

FIGS. 17a-17c illustrate motion corrupted magnitude and the corresponding phase images of the slice 7 in different diffusion encoding directions are compared with respect to motion free shot. Phase-encoding was in horizontal direction. The solid and the dotted circles represent the accepted and the rejected measurements, respectively. The numeric numbers enclosed within the rectangular boxes represent the different slices in a given repetition time TR. The numbers enclosed within the circle in FIG. 17a and FIG. 17c indicate the different diffusion encoding directions, which includes 0 for b=0 s/mm², and those in the rectangular boxes are for the different slices. The data, which failed the RTN test and therefore is rejected, is indicated by the number encircled by the dotted lines, and the accepted data are enclosed by the solid circles. From Fourier transform theory, one pixel shift in k space corresponds to 2π phase difference on the edge of FOV in image space. The number of the wraps in phase images represents the number of shift of $\Delta k_x$ in k-space. The shots that either the magnitude of the navigator changed more than 30% or the k=0 peak shifted more than 2·$\Delta k_x$ (=2/FOV$_x$) from the reference values were reacquired.

The measured raw data was transferred from the scanner to a computer for further analysis. The magnitude image for diffusion encoding direction 2 indicated substantial reduction compared to other directions (3 and 4). This shot was rejected and reacquired in real-time. The reacquired image encircled by solid line for direction 2 demonstrated no motion artifact.

For direction 3, although the first attempt for slice 7 succeeded for the RTN test as in the figure, RTN reported the failure on this measurement, because other slices ($S_1$ and $S_3$) failed the test as indicated in FIG. 3b and 3d. k=0 peaks of the slices 1 and 3 shifted by 3$\Delta k_y$ and 2$\Delta k_y$, respectively. Therefore, the whole acquisition of direction 3 was repeated.

Figure 18:
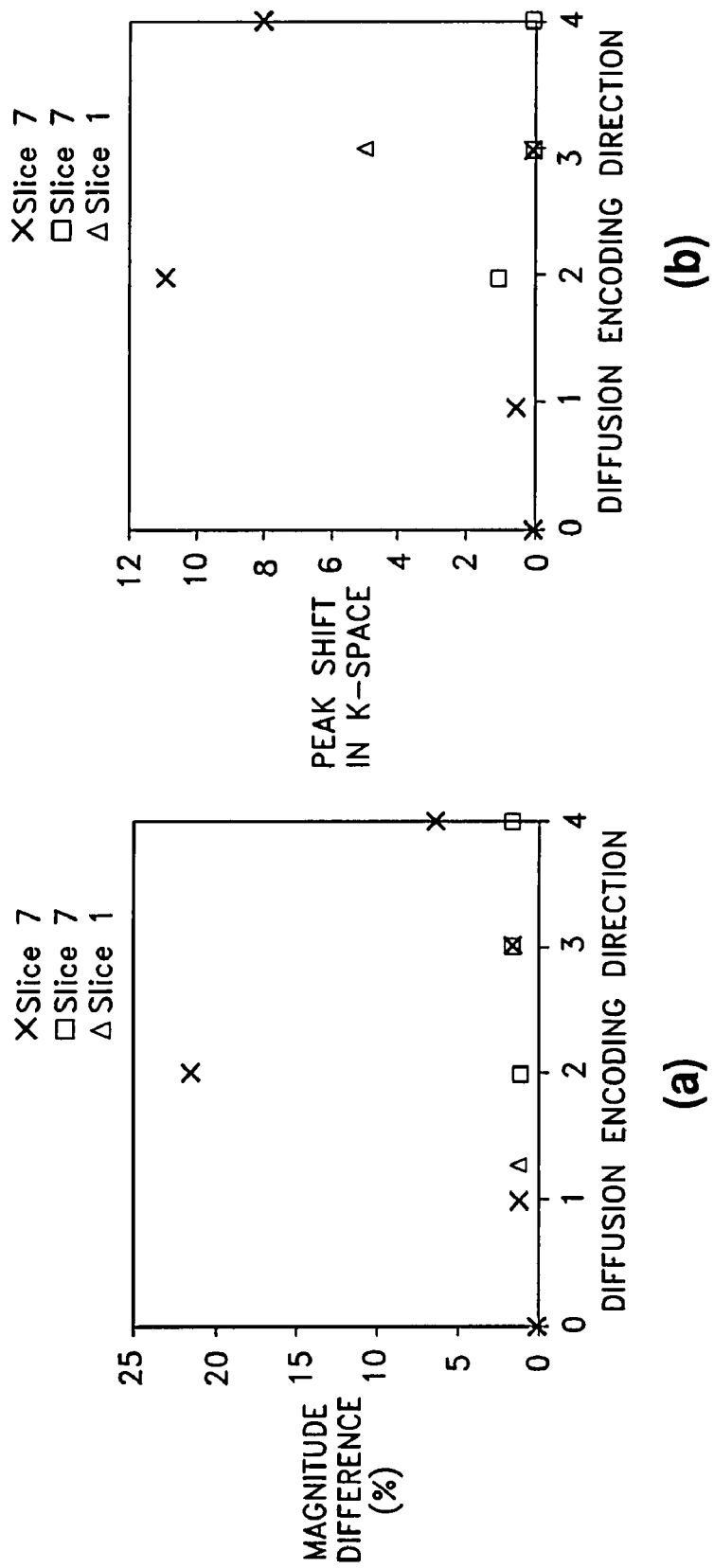
FIG. 18 is a plot of echo-peak position in k-space along various diffusion encoding directions of b=0 and 400 s/mm².

FIGS. 18a and 18b illustrate plots of the echo-peak position in k-space along various diffusion encoding directions of b=0 and 400 s/mm². Numbers in horizontal axis represent b=0, (1,0,0), (0,1,0), (0,0,1), and (1,1,1). The shift was plotted separately along the readout and phase-encoding directions. The change of the magnitude and the peak shift of the largest echo in 2D navigator are plotted in FIGS. 18a and 18b, respectively. The numbers in horizontal axis represent the diffusion encoding directions, which includes 0 for b=0. The shift of the echo peak was calculated from the peak position of the reference navigator echo. When the phantom was moved along phase-encoding direction, the peak shift occurred in $k_y$ direction, while it was observed in $k_x$ or the motion along the readout direction. As indicated in the direction 2 in FIGS. 17a and 17c, the magnitude was decreased by 22.5% and k=0 peak shifted about 11 units of Δk in phase-encoding direction.

Figure 19:
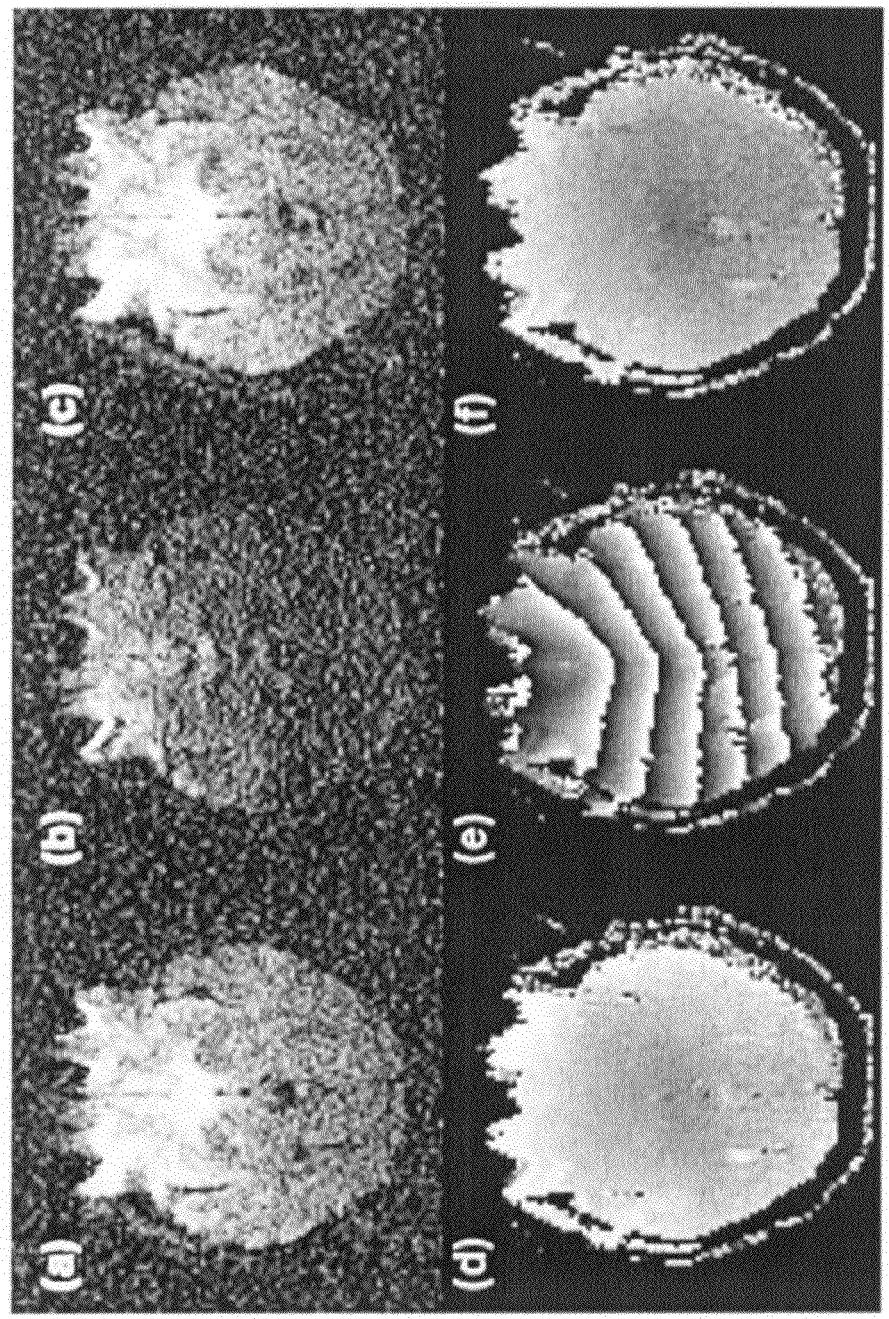
FIG. 19 depicts magnitude (a-c) and corresponding phase images (d-f) of healthy human brain.

FIG. 19 illustrates the magnitude and the phase images of (a, d) the reference (the first average), (b, e) the motion-corrupted, and (c, f) the reacquired data in DW imaging of a human volunteer. The volunteer intentionally nodded his head to initiate the rotational motion during the acquisition of corrupted shot. The corrupted and reacquired images clearly indicated the significant drop of the magnitude in FIG. 19b and the improvement in FIG. 19c, respectively. RTN test reported 52% change of the magnitude and 7 Δk shift of the navigator peak for this specific data in FIG. 19(b, e) compared to the first averaging data in in FIG. 19(c, f). This shot failed both magnitude and shift tests.

Figure 20:
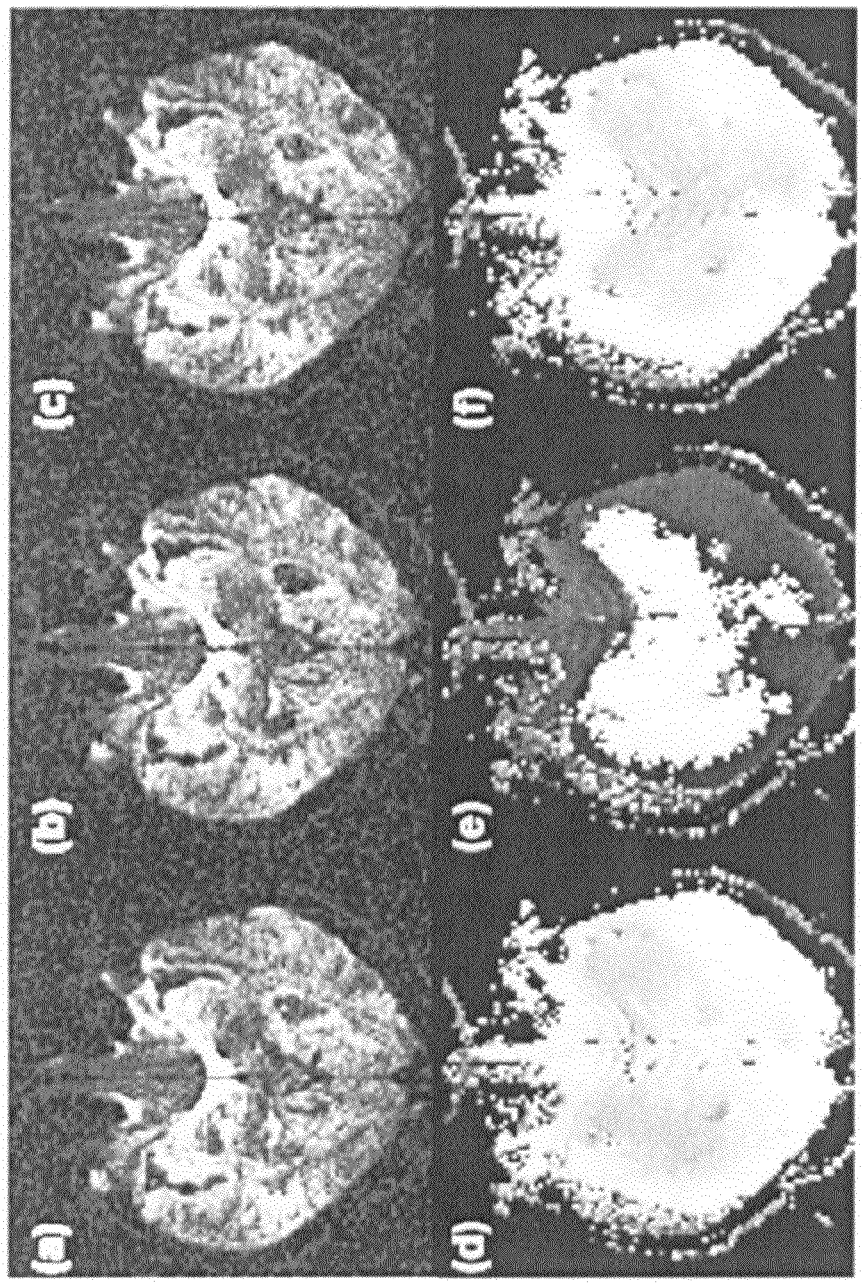
FIG. 20 shows results of real time navigated DW imaging for a typical corporative subject.

The motion artifact in FIGS. 19a, b is an exceptional case of motion, which was caused by intentional head motion, and which will be of a greater magnitude than that normally encountered when imaging a patient endeavoring to remain still. Because the source of motion artifact for most of corporative human subjects may be breathing and swallowing motions, all others data were much cleaner than these images. The images in FIG. 20 are from a volunteer, who stayed still during the entire DW imaging acquisition except a few swallowing motion. The images in FIG. 20 are the magnitude and the phase images of (a, d) the reference (the first average), (b, e) the motion-corrupted, and (c, f) the reacquired data. RTN process reported the magnitude change below 0.5% and 2 Δk shift of the navigator peak echo. This shot succeeded the magnitude test, however it failed for the phase test and the entire slices were reacquired in real-time.

Intra-shot motion particularly during the application of the diffusion gradients can cause a significant signal loss when even small motion can cause partial or complete dephasing or an additional phase factor in image space. The motion caused by global changes in subject position results in additional phase term in k-space data (translation) or k-space data shift (rotation). Both types of motion can be identified by using the navigator data.

Once the motion corruption occurs within the DW images, it is difficult to correct the artifact. As described herein, 30% for magnitude variation and 2 $\Delta k_x$ for the peak shift of k=0 point in k-space were used for the acceptable criterions. Either/both decreasing the magnitude change or/and increasing the peak shift will increase the imaging time, which can induce the increased chance of the position change among the shots. Limits on the number of reacquisition of a specific set of measurements can be specified to 2 for imaging of both the phantom and the brain of human volunteer to avoid unacceptably long acquisitions. It may be increased to image the subjects who may be somewhat corporative. However the increased maximum reacquisition may extend the total imaging time for incorporative patients, because there may be frequent failure of RTN test for all diffusion encodings. The bounds for these values may be based on the ranges that yield minimal artifact and minimal reduction in DTI accuracy in minimal increase of the acquisition time.

During the preliminary imagings, there were occasions which the maximum reacquisition count was consumed without passing the RTN test and the acquisition proceeded to the next acquisition. The acquisition with the least change of the magnitude and the position of the largest echo peak was selected for averaging in offline, using the measurement raw data. This algorithm may be implemented into the online reconstruction program.

If the subject moves and the data are corrupted while acquiring the first average, all subsequent repetitions may fail to pass the acceptance criteria. Then the acquisition may be stopped and the subject may be instructed to hold still and the acquisition may be restarted.

Upon using multi-channel receive-only coil, the channel closed to the region of interest was selected for RTN evaluation. For instance, a channel in the posterior matrix element can be selected for DTI of cervical spinal cord. For multi-slice imaging, the comparison is made slice-by-slice. If the navigator echoes for given number of slices cannot satisfy the acceptance criteria, this shot is reacquired.

There is a minimum duration for RTN process which includes the real-time data communication between the acquisition and the reconstruction computers and the calculation in the reconstruction computer. This delay must be increased with the increased complexity of the calculation, such as including Fourier-transformation. It reduces the maximum number of slices for a given TR. 1 ms was long enough for current study because the process in real-time ICE program was simple.

If the motion of the imaging subject caused the change of position from previous averages and occurred between the shots, RTN would not be able to detect because the there would not be significant change in the magnitude and in the position of the navigator echo peak. The RTN algorithm may be modified such that the Fourier-transformed magnitude image is subtracted from the reference image and the total signal of the difference image is summed up and used to detect the change of the position which may have occurred in between the current and previous shots. The RTN may not reject these data; rather a postprocessing may be used to co-register the later averages with respect to the early ones before the magnitude averaging.

In multishot diffusion MRI, navigator echoes are used to correct the instability of the phase error among the data for different segments, which include the self-navigating techniques such as SNAIL (self-navigated interleaved spiral) and PROPELLER (periodically rotated overlapping parallel lines with enhanced reconstruction) that use the imaging echoes as the navigator to directly monitor the acquired data. These imaging techniques use the navigator echoes in post-processing, not in real-time. Real-time navigation has been used to directly measure the fat signal within the FOV in cardiac imaging. The RTN technique can be implemented into a multishot DWEPI sequence by acquiring an addition echotrain that samples 8~16 echoes of the center of k-space.

RTN imaging is more suitable to identify global rather than local motion. It can be also used to detect and monitor voluntary local motion such as swallowing, which induced the shift of the navigator peak by a few Δk, as demonstrated in images in FIG. 20. It may be acceptable for DTI of brain. However, swallowing may induce the anterior-posterior motion on DTI of the cervical spinal cord. Because the swallowing does not happen frequently, the RTN parameters may be set to screen any motion with equal or larger amplitude than the swallowing. If the selected coil segment is sensitive to a local motion, such as a CSF pulsation for DWI of cervical spinal cord, RTN test may fail more often that is desirable. In these cases however, the RTN technique may be combined with cardiac gated acquisition for diffusion-weighted imaging. Since each reacquisition increases the total imaging time by TR, the threshold values for magnitude change and the peak shift of the 2D navigator echoes for RTN may be increased to detect the data corruption due to the large motion only and to reduce the number of failures in RTN test.

As a result, real-time navigated data acquisition for diffusion-weighted imaging improve the DTI measurement result by identifying and reacquiring the data with excessive motion-related corruption in real-time. It can be used to reduce the inconsistency among the different averaging caused by subject motion during the application of the diffusion gradients and/or between shots and, therefore, improves the accuracy of DTI measurements. This technique can be particularly useful to detect the global motion of the imaging region.

While certain aspects and embodiments have been described, these have been presented by way of example only, and are not intended to limit the scope of this disclosure. Indeed, the novel methods and systems described herein may be embodied in a variety of other forms without departing from the spirit thereof. The accompanying claims and their equivalents are intended to cover such forms or modifications as would fall within the scope and spirit of this disclosure.

What is claimed is:

1. A method for operating an MRI system in diffusion imaging, comprising the steps of:
    providing a single Diffusion-Prepared Driven-Equilibrium preparation (DPDE) for a localized imaging volume comprising a first excitation RF pulse followed by first and second successive RF inversion pulses, said first and second successive RF inversion pulses determining the localized imaging volume for imaging with the first inversion pulse inverting magnetization and the second inversion pulse and accompanying phase encoding gradient restoring magnetization to a non-selected portion of said localized imaging volume;
    acquiring Diffusion-weighted MRI imaging (DWI) and Diffusion-tensor MRI imaging (DTI) 3-dimensional k-space data from the prepared localized imaging volume by applying a plurality of stimulated echo planar imaging (EPI) pulse sequence acquisitions of a selected portion of said localized imaging volume, in response to said single diffusion-prepared driven-equilibrium preparation; and
    reconstructing and generating medical images of said localized imaging volume using the acquired DWI and DTI 3-dimensional k-space data, in response to said single diffusion-prepared driven-equilibrium preparation.

2. The method of claim 1, wherein
    the selected portion of said localized imaging volume comprises a slab being imaged and said plurality of stimulated echo planar imaging pulse sequence acquisitions acquire said slab as center-out k-space segments and
    said first excitation RF pulse and the first and second successive RF inversion pulses comprise 90 degree, 180 degree and 180 degree pulses respectively.

3. The method of claim 1, wherein said plurality of stimulated echo planar imaging pulse sequence acquisitions acquire interleaved k-space segments and employ a corresponding plurality of variable flip angle RF excitation pulses progressively changed to reduce $T_1$ decay-related blurring in a slice direction.

4. The method of claim 1, wherein said MRI system is operated for diffusion-weighted MR imaging (DWI) and said plurality of stimulated echo planar imaging pulse sequence acquisitions acquire a plurality of interleaved k-space segments with an individual segment being acquired using an excitation RF pulse, rephasing crusher gradient, an echo-planar imaging readout gradient, and a rewinding or spoiler gradient.

5. The method of claim 1, wherein said MRI system is operated for diffusion tensor MR imaging (DTI).

6. The method of claim 1, wherein the step of acquiring 3-dimensional k-space data comprises center-out acquisition of 3-dimensional k-space data segments for reconstruction of an individual image slice, in response to said single diffusion-prepared driven-equilibrium preparation.

7. A control system for an MRI apparatus for use in diffusion imaging, comprising:
    a control processor configured to generate one or more instructions for:
        providing a single Diffusion-Prepared Driven-Equilibrium (DPDE) for a localized imaging volume comprising a first excitation RF pulse followed by first and second successive RF inversion pulses, said first and second successive RF inversion pulses determining the localized imaging volume with the first inversion pulse inverting magnetization and the second inversion pulse and accompanying phase encoding gradient restoring magnetization to a non-selected portion of said localized imaging volume;
        acquiring 3-dimensional Diffusion-weighted MRI imaging (DWI) and Diffusion-tensor MRI imaging (DTI) k-space data from the prepared localized imaging volume by applying a plurality of stimulated echo planar imaging (EPI) pulse sequence acquisitions of a selected portion of said localized imaging volume, in response to said single diffusion-prepared driven-equilibrium preparation; and
    reconstructing and generating medical images of said localized imaging volume using the acquired DWI and DTI 3-dimensional k-space data, in response to said single diffusion-prepared driven-equilibrium preparation.

8. The system of claim 7, wherein
    the selected portion of said localized imaging volume comprises a slab being imaged and said plurality of stimulated echo planar imaging pulse sequence acquisitions acquire said slab as center-out k-space segments and
    said first excitation RF pulse and the first and second successive RF inversion pulses comprise 90 degree, 180 degree and 180 degree pulses respectively.

9. The system of claim 7, wherein said plurality of stimulated echo planar imaging pulse sequence acquisitions acquire interleaved k-space segments and employ a corresponding plurality of variable flip angle RF excitation pulses progressively changed to reduce $T_1$ decay-related blurring in a slice direction.

10. The system of claim 7, wherein said MRI apparatus is for diffusion-weighted MR imaging (DWI) and said plurality of stimulated echo planar imaging pulse sequence acquisitions acquire a plurality of interleaved k-space segments with an individual segment being acquired using an excitation RF pulse, rephasing crusher gradient, an echo-planar imaging readout gradient, and a rewinding or spoiler gradient.

11. The system of claim 7, wherein said MRI apparatus is configured for diffusion tensor MR imaging (DTI).

12. The system of claim 7, wherein said acquiring of 3-dimensional k-space data comprises center-out acquisition of 3-dimensional k-space data segments for reconstruction of an individual image slice, in response to said single diffusion-prepared driven-equilibrium preparation.

* * * * *

UNITED STATES PATENT AND TRADEMARK OFFICE
CERTIFICATE OF CORRECTION

PATENT NO. : 8,406,849 B2
APPLICATION NO. : 11/732382
DATED : March 26, 2013
INVENTOR(S) : Eun-Kee Jeong et al.

Page 1 of 1

It is certified that error appears in the above-identified patent and that said Letters Patent is hereby corrected as shown below:

In the specification

In Column 1, lines 15-20, under Government License Rights,

"The U.S. Government has a paid-up license in this invention and the right in limited circumstance to require the patent owner to license others on reasonable terms as provided for by the terms of Grant Nos. R21 NS052424, R21 EB005705, and R01 HL057990 awarded by the National Institutes of Health" should read --This invention was made with government support under R01 HL057990, R21 EB005705 and R21 NS052424 awarded by The National Institutes of Health. The government has certain rights in the invention.--

Signed and Sealed this
Thirty-first Day of May, 2016

Michelle K. Lee
*Director of the United States Patent and Trademark Office*